United States Patent [19]

Shiraishi et al.

[11] Patent Number: 5,162,571

[45] Date of Patent: Nov. 10, 1992

[54] PHENOL DERIVATIVES, THEIR PRODUCTION AND USE

[75] Inventors: Mitsuru Shiraishi, Suita; Kohei Mishikawa, Kyoto, both of Japan

[73] Assignee: Takeda Chemical Industries, Ltd., Osaka, Japan

[21] Appl. No.: 204,530

[22] Filed: Jun. 8, 1988

[30] Foreign Application Priority Data

Jun. 9, 1987 [JP] Japan .................. 62-144506

[51] Int. Cl.$^5$ ...................... C07C 69/76; A01N 37/10
[52] U.S. Cl. .................... 514/237.5; 560/45; 560/53; 560/57; 560/455; 560/463; 560/468; 560/459; 544/171; 544/172; 546/225; 548/547; 549/14; 549/375; 514/255
[58] Field of Search .................. 560/57, 53, 45; 562/455, 463, 468; 544/171, 172; 546/225; 548/547; 549/14, 375; 514/236, 330, 433, 532, 533, 570

[56] References Cited

U.S. PATENT DOCUMENTS 2,933,523  4/1960  Greenlee ................ 260/520
3,058,946 10/1962  Nametz .................. 260/42
3,471,537 10/1969  Berke ................... 260/429

FOREIGN PATENT DOCUMENTS 0171251  2/1986  European Pat. Off. .
2701280  7/1978  Fed. Rep. of Germany .
61-148144 7/1986  Japan .
61-148174 7/1986  Japan .
61-183264 8/1986  Japan .

Primary Examiner—Paul J. Killos
Attorney, Agent, or Firm—Wenderoth, Lind & Ponack

[57] ABSTRACT

Novel phenol derivatives of the general formula:

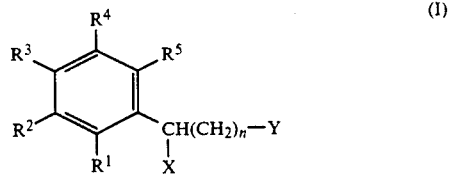

(I)

wherein $R^1$, $R^2$, $R^3$, $R^4$, $R^5$, X, Y and n are as defined in the specification, which have therapeutic and prophylactic activities against cerebral, cardiac, renal and pulmonary circulatory system diseases, respiratory diseases, allergy, anaphylactic shock, endotoxin shock, inflammation and the like as well as inhibiting activities against vascularization by oncocytes.

16 Claims, No Drawings

PHENOL DERIVATIVES, THEIR PRODUCTION AND USE

FIELD OF THE INVENTION

The present invention relates to novel phenol derivatives, their production and use. The novel phenol derivatives of the present invention have therapeutic and prophylactic activities against cerebral, cardiac, renal and pulmonary circulatory system diseases, respiratory diseases, allergy, anaphylactic shock, endotoxin shock, inflammation and the like as well as inhibiting activities against vascularization by oncocytes.

BACKGROUND OF THE INVENTION

It has been shown that thromboxane $A_2$, leukotrienes and active oxygen are greatly responsible for making a basal lesion worse and any excess production thereof can become an impairment factor to the living body. For example, thromboxane $A_2$ is mainly synthesized from arachidonic acid in blood platelets and leukocytes and it has been known that it has strong platelet aggregation activity and constriction activity against a blood vessel and bronchial smooth muscle. And, it has been considered that excess production of thromboxane $A_2$ and imbalance in production of thromboxane $A_2$ and prostacycline cause thrombosis, myocardial infarction, cerebral infarction, peptic ulcer, asthma, cerebral edema, arterial sclerosis, hepatic diseases, renal diseases and the like. Further, it has been considered that leukotrienes are strong chemical mediators of allergic or inflammatory responses and thereby they mainly cause pulmonary periphery airway constriction and pertain to dyspnea accompanied with bronchial asthma. Leukotrienes have capillary permeability sthenic and strong leukocyte migratory abilities and thereby they also deeply pertain to edema or cell humectation which is one of the main symptoms of inflammation. Strong constriction activities against a blood vessel and cardiac muscle exerted by leukotriene $C_4$ are considered to be responsible for coronary insufficiency and angina pectoris.

Furthermore, among prostanoides, prostaglandin $H_2$, prostaglandin $D_2$, prostaglandin F $2\alpha$ or 11-epi-prostaglandin F $2\alpha$ which exerts constriction activities against a blood vessel and bronchial smooth muscle has been noted with respect to clarification of its participation in the above diseases.

Recently, it has been made clear that a kind of active oxygen plays an important role as an impairment factor in the progress of a lesion in an ischemic tissue [I. Fridovich, Annual. Review of Pharmacology and Toxicology, 23, 239 (1983); J. M. McCord and G. Ghai, American Journal of Physiology, 246, H776 (1984)]. It is considered that superoxide, hydroxyl radical, singlet oxygen, peroxide radical and the like are included in this kind of active oxygen in the living body. Particularly, it is considered that, in formation of superoxide in the living body and subsequent impairment of cells or a tissue by the active oxygen, excess production of superoxide has an important significance as a substantial factor.

Accordingly, there have been advanced synthetic studies of substances for antagonizing the receptor of eicosanoides such as thromboxan $A_2$, prostaglandin $H_2$, prostaglandin $D_2$ and the like involved in arachidonic acid cascade; substances for inhibiting 5-lipoxygenase which is an incipient enzyme for biosynthesis of leukotrienes; substances for eliminating active oxygen or inhibiting formation of active oxygen; and the like. For example, in Japanese Patent Laid Open Publication Nos. 61-148144, 61-148174 and 61-183264, there are disclosed certain benzene derivatives having anti-peroxidized fat activities.

OBJECTS OF THE INVENTION

One object of the present invention is to provide novel phenol derivatives which have active oxygen eliminating activity together with antagonistic activity to the receptor of eicosanoides such as thromboxan $A_2$, prostaglandin $H_2$, prostaglandin $D_2$ and the like or 5-lipoxygenase inhibiting activity and thereby have therapeutic and prophylactic activities against cerebral, cardiac, renal and pulmonary circulatory system diseases, respiratory diseases, allergy, anaphylactic shock, endotoxin shock, inflammation and the like as well as inhibiting activities against vascularization by oncocytes.

Another object of the present invention is to provide a process for producing the phenol derivatives.

Still another object of the present invention is to provide a pharmaceutical composition useful for treating, preventing and inhibiting the above diseases which contains the phenol derivatives.

These objects as well as other objects and advantages of the present invention will become apparent to those skilled in the art from the following description.

DESCRIPTION OF THE INVENTION

The phenol derivative of the present invention is represented by the general formula:

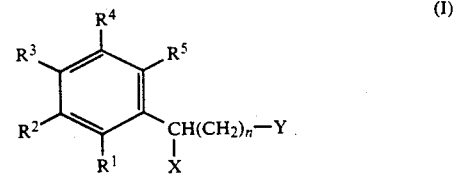

(I)

wherein $R^1$ is an optionally protected hydroxy group; $R^2$ is hydrogen atom, hydroxy group, a lower alkyl group or a lower alkoxy group; $R^3$ is hydrogen atom, hydroxy group, an optionally substituted alkyl group having 1 to 8 carbon atoms, an optionally substituted aralkyl group, a halogen atom, an optionally protected formyl group, an acyl group having 2 to 7 carbon atoms, an optionally esterified or amidated carboxyl group, $-CH=CHR^6$ group (wherein $R^6$ is a lower alkyl group or a lower acyl group) or $-CH=-R^7$ (wherein $R^7$ is hydroxy group, a lower alkoxy group, a lower alkenyloxy group or benzhydryloxy group); $R^4$ is an optionally substituted alkyl having 1 to 8 carbon atoms, an optionally substituted aralkyl group, a halogen atom, an optionally protected formyl group, an acyl group having 2 to 7 carbon atoms, an optionally esterified or amidated carboxyl group, $-CH=CHR^6$ (wherein $R^6$ is as defined above) or $-CH=NR^7$ (wherein $R^7$ is as defined above); $R^5$ is hydrogen atom or a lower alkyl group; or two adjacent groups of $R^2$, $R^3$, $R^4$ and $R^5$ may bond to each other to form $-(CH_2)_a-$ group (wherein a is 3 or 4), $-CH=CH-CH=CH-$ group, $-(CH_2)_b-CO-$ group (wherein b is 2 or 3) or $-(CH_2)_l-CO-O-$ group (l is 1 or 2); X is phenyl group optionally substituted with a halogen atom, a lower alkyl group or a lower alkoxy group at the para-position thereof or thienyl group; Y is methyl group, an optionally substituted hydroxymethyl group, an optionally esterified or amidated carboxyl group, cyano group or tetrazolyl group; and n is an integer of 3 to 15.

Examples of the optionally substituted hydroxy group in $R^1$ of the novel phenol derivatives represented by the general formula (I) of the present invention include hydroxy group, a lower alkoxy group having 1 to 4 carbon atoms (e.g., methoxy, ethoxy, propoxy), methoxymethyloxy, benzyloxy, a lower acyloxy group having 1 to 4 carbon atoms (e.g. formyloxy, acetoxy, propionyloxy), tetrahydropyranyloxy and the like.

Examples of the lower alkyl group represented by $R^2$ include alkyls having 1 to 4 carbon atoms such as methyl, ethyl, propyl, isopropyl, butyl, isobutyl, t-butyl and the like. Examples of the lower alkoxy group, include alkoxy having 1 to 4 carbon atoms such as methoxy, ethoxy, propoxy, isopropoxy, butoxy, isobutoxy, t-butoxy and the like.

Examples of the optionally substituted alkyl group having 1 to 8 carbon atoms represented by $R^3$ and $R^4$ include unsubstituted alkyl groups such as methyl, ethyl, propyl, isopropyl, butyl, isobutyl, t-butyl, pentyl, hexyl, heptyl, octyl and the like as well as these alkyl groups substituted with one or more hydroxy groups, alkoxy groups as defined with respect to $R^2$, halogen atoms (e.g., fluorine, chlorine, bromine) and/or carboxyl groups (e.g., hydroxymethyl, 1-hydroxyethyl, 2-hydroxyethyl, carboxymethyl, 2-carboxyethyl, methoxymethyl, trifluoromethyl, chloromethyl, etc.). Examples of the optionally substituted aralkyl group include one having 7 to 13 carbon atoms such as benzyl, 1-phenylethyl, 2-phenylethyl, diphenylmethyl and the like and these groups may have 1 to 5 substituents, preferably 1 to 3 substituents at any positions thereof. As such substituents, for example, there are halogen atoms such as fluorine, chlorine, bromine and the like. Examples of the halogen atom represented by $R^3$ and $R^4$ include fluorine, chlorine, bromine and the like. As the acyl group having 2 to 7 carbon atoms, there are alkylcarbonyls such as acetyl, propionyl, butyryl, valeryl and the like. As the optionally protected formyl group represented by $R^3$ and $R^4$, in addition to unsubstituted formyl group, there are, for example, 1,3-dioxolan, propylene acetal, 1,3-oxathiolan, dialkyl acetal (the alkyl having 1 to 4 carbon atoms) and the like. As the esterified carboxyl group represented by $R^3$ and $R^4$, there are lower alkoxycarbonyl having 2 to 5 carbon atoms (e.g., methoxycarbonyl, ethoxycarbonyl, etc.), aralkyloxycarbonyl having 8 to 10 carbon atoms (e.g., benzyloxycarbonyl, etc.) and aryloxycarbonyl having 7 to 10 carbon atoms (e.g., phenoxycarbonyl, 4-methylphenyloxycarbonyl, 4-methoxyphenyloxycarbonyl, etc.). As the amidated carbonyl group represented by $R^3$ and $R^4$, in addition to unsubstituted aminocarbonyl, there are substituted aminocarbonyl in which the amino group is substituted with hydroxyl or alkyl having 1 to 4 carbon atoms (e.g., methylaminocarbonyl, ethylaminocarbonyl, i-propylaminocarbonyl, dimethylaminocarbonyl, hydroxyaminocarbonyl, etc.) and cyclic aminocarbonyl (e.g., morpholinocarbonyl, piperidinocarbonyl, pyrrolidinocarbonyl, piperazinocarbonyl, etc.). The cyclic aminocarbonyl may have alkyl having 1 to 2 carbon atoms or alkoxy having 1 to 2 carbon atoms at an optional position on the ring.

Examples of the lower alkyl group represented by $R^5$ and $R^6$ include those as defined with respect to the above $R^2$. And, as the lower acyl group represented by $R^6$, there are ones having 2 to 6 carbon atoms such as acetyl, propionyl, butyryl and the like.

Examples of the lower alkoxy group represented by $R^7$ include ones having 1 to 8 carbon atoms such as methoxy, ethoxy, propoxy, i-propoxy, butoxy, pentyloxy, hexyloxy, octyloxy and the like. And, as the lower alkenyloxy group, for example, there are ones having 2 to 6 carbon atoms such as ethenyloxy, 1-propenyloxy, 2-propenyloxy, 1-butenyloxy, 2-butenyloxy and the like.

Examples of halogen atoms as the substituents of phenyl represented by X include those as defined with respect to the above $R^3$. Examples of the lower alkyl groups as the substituents of phenyl represented by X include those as defined with respect to the above $R^2$. Examples of the lower alkoxy groups as the substituents of phenyl represented by X include those as defined with respect to $R^2$.

Hydroxymethyl group represented by Y may be substituted and, in addition to unsubstituted hydroxymethyl group, examples thereof include methoxymethyl, acetoxymethyl, 2-tetrahydropyranyloxymethyl, benzyloxymethyl, nitroxymethyl, aminocarbonyloxymethyl, substituted aminocarbonyloxymethyl (e.g., methylaminocarbonyloxymethyl, ethylaminocarbonyloxymethyl, dimethylaminocarbonyloxymethyl, phenylaminocarbonyloxymethyl, etc.), cyclic aminocarbonyloxymethyl (e.g., morpholinocarbonyloxymethyl, piperidinocarbonyloxymethyl, pyrrolidinocarbonyloxymethyl, piperazinocarbonyloxymethyl, etc.), t-butyldimethylsilyloxymethyl and the like. As the esterified carboxyl group, for example, there are lower alkoxycarbonyl having 2 to 4 carbon atoms such as methoxycarbonyl, ethoxycarbonyl and the like. The amidated carboxyl group represented by Y may be a substituted aminocarbonyl in which the amino group is substituted, or may be cyclic aminocarbonyl. As the substituent of the amino group of the substituted aminocarbonyl, for example, there are alkyl having 1 to 4 carbon atoms such as methyl, ethyl, propyl, isopropyl, butyl and the like, aryl having 6 to 10 carbon atoms such as phenyl, naphthyl and the like (they may further have one or more substituents such as hydroxy, amino, nitro, halogen, methyl, methoxy, etc. at optional positions), hydroxy and the like. Specific examples of the amidated carboxyl group include aminocarbonyl; mono- or dialkylamino-(e.g., methylamino-, ethylamino-, isopropylamino-, dimethylamino-)carbonyl; aralkylamino-[e.g., benzylamino-, α-phenethylamino-, β-phenethylamino-, 1-(α- naphthyl)ethylamino-]carbonyl; phenylaminocarbonyl; substituted phenylamino-(e.g., p-hydroxyphenylamino-, p-methoxyphenylamino-, m-chlorophenylamino-, p-bromophenylamino-)carbonyl; diphenylaminocarbonyl; hydroxyaminocarbonyl; N-hydroxy-N-methylaminocarbonyl; N-hydroxy-N-phenylaminocarbonyl; an amino acid residue in which one hydrogen is removed from the corresponding amino acid (e.g., glycine residue, arginine residue, histidine residue, asparagine residue, proline residue, phenylalanine residue, alanine residue, methionine residue, leucine residue)carbonyl; and the like. As the cyclic aminocarbonyl, for example, there are morpholinocarbonyl, piperidinocarbonyl, pyrrolidinocarbonyl, piperazinocarbonyl and the like.

Among the phenol derivatives represented by the general formula (I) of the present invention, those wherein X is phenyl, 4-methylphenyl, 4-fluorophenyl, 2-thienyl, 3-thienyl, etc., Y is carboxyl and the number of methylene groups (n) is 5 to 9 are preferred from the viewpoint of their pharmacological activities.

The novel phenol derivative represented by the general formula (I) of the present invention can be produced by reacting a compound of the general formula:

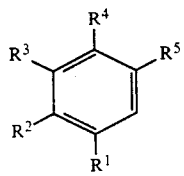

wherein $R^1$, $R^2$, $R^3$, $R^4$ and $R^5$ are as defined above, with a compound of the general formula:

$$A-CH(CH_2)_n-Y$$
$$|$$
$$X$$
(III)

wherein X, Y and n are as defined above, and A is hydroxy group, acetoxy group, a lower alkoxy group such as that described above or a halogen atom. Usually, this reaction can be carried out by condensation of the reactants in the presence of an acid catalyst. For example, this condensation reaction can be carried out in a nonpolar solvent such as methylene chloride, chloroform, 1,2-dichloroethane, benzene, toluene, 1,1,2,2,-tetrachloroethane or the like at a temperature of 10° to 110° C. in the presence of an acid catalyst such as boron trifluoride ethyl ether, aluminum chloride, zinc chloride, p-toluene sulfonic acid, D-camphor sulfonic acid or the like. Particularly, this condensation reaction depends upon the solubility in the solvent of the compound (II) and the reactivity of the acid catalyst with the compound (III). Therefore, it is preferred to change the reaction catalyst according to a particular combination of the compounds (II) and (III), and the amount of the acid catalyst to be used is preferably in the range of about 1/20 to 1 mole based on the compound (II) to be used. Preferably, this reaction is carried out in the absence of oxygen.

The compound (II) to be used as the starting material is known or produced by a process as disclosed in Reference Examples hereinafter. The compound (III) is also known or produced according to a known process.

Alternatively, the compound of the general formula (I) wherein Y is carbamoyloxymethyl group, N-substituted carbamoyloxymentyl group, hydroxyaminocarbonyl group, N-substituted hydroxyaminocarbonyl group, hydroxymethyl group, carboxyl group, alkoxycarbonyl group, aminocarbonyl group, substituted aminocarbonyl group, cyano group or tetrazolyl group can be produced from the compound wherein Y is hydroxymethyl group, carboxyl group, alkoxycarbonyl group or acyloxymethyl group according to the reactions as shown in Scheme 1 which themselves are known.

Scheme 1

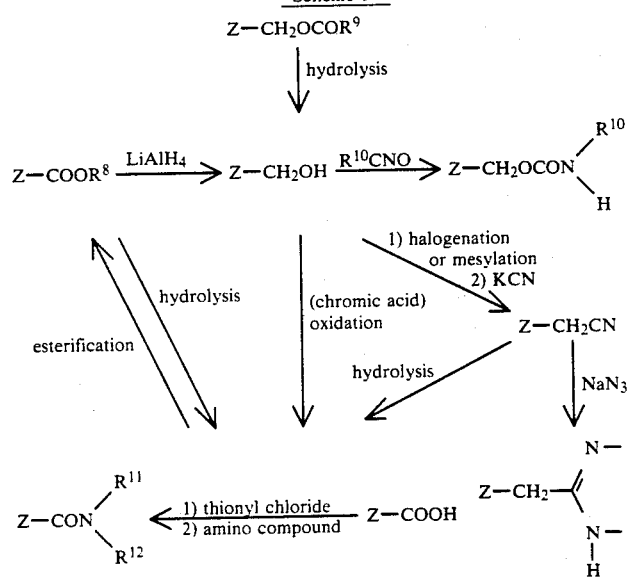

In Scheme 1, Z is a group represented by the formula:

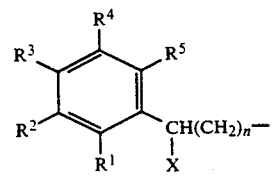

wherein $R^1$, $R^2$, $R^3$, $R^4$, $R^5$, X and n are defined above; $R^8$ and $R^9$ are an alkyl group having 1 to 3 carbon atoms; $R^{10}$ is hydrogen atom, an alkyl group having 1 to 6 carbon atoms or an aryl group; and $R^{11}$ and $R^{12}$ are hydrogen atom, a lower alkyl group having 1 to 6 carbon atoms, hydroxy group, a lower alkoxy group having 1 to 6 carbon atoms or an aryl group provided that at least one of $R^{11}$ and $R^{12}$ is a group other than hydroxy group or an alkoxy group having 1 to 6 carbon atoms.

Further, among the phenol derivatives represented by the general formula (I), those wherein $R^2$ is hydrogen atom, a lower alkyl group or a lower alkoxy group; and $R^3$ is hydrogen atom or a lower alkyl group can also be produced from the corresponding compounds wherein $R^4$ is unsubstituted according to the reactions as shown in Scheme 2 which themselves are known.

wherein Y is free carboxyl group exert antagonistic activities to the receptor of eicosanoides such as thromboxane $A_2$, prostaglandin $H_2$, prostaglandin $D_2$ and the

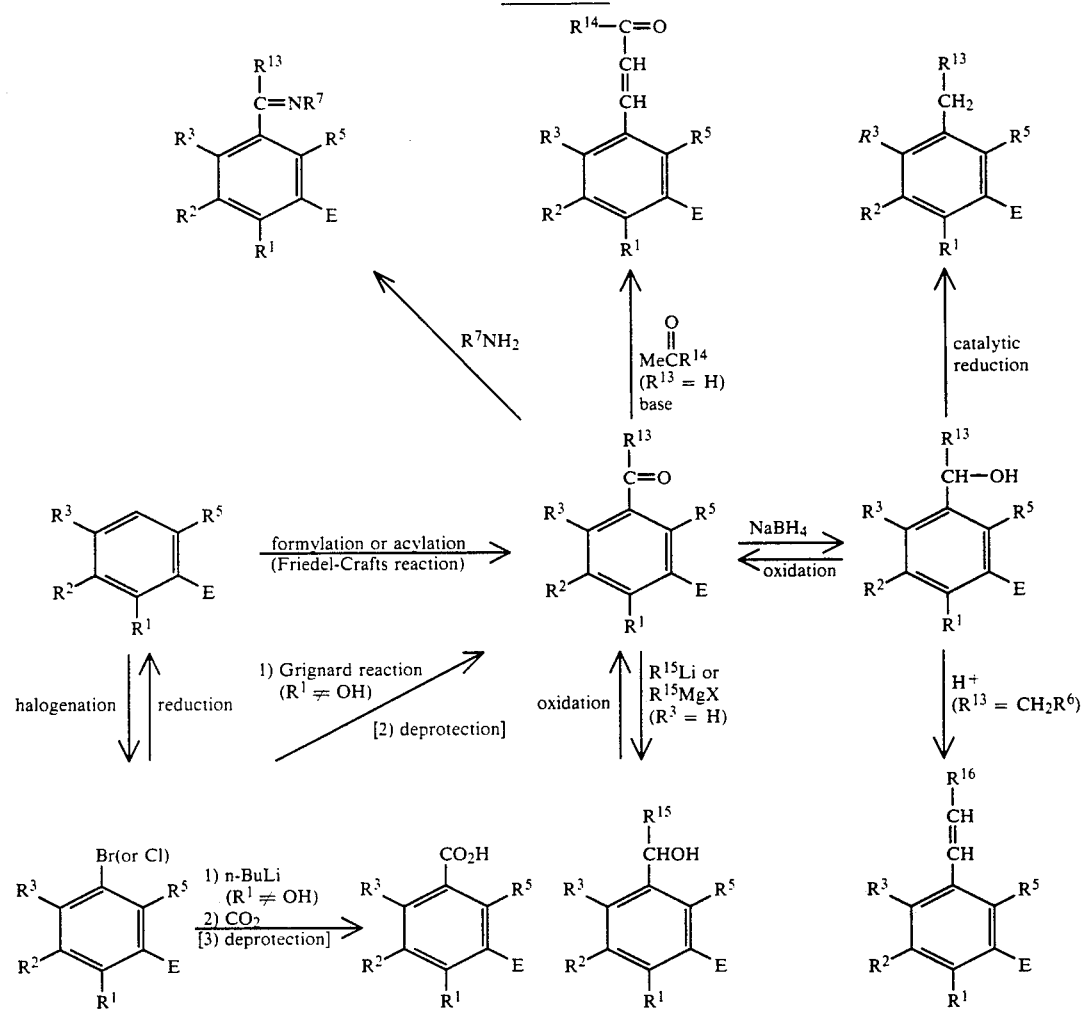

Scheme 2

Further, in Scheme 2, when $R^1$ is a protected hydroxy group, the protecting group can be removed by subjecting the resultant compound to acid hydrolysis or catalytic reduction which itself is known after completion of the reaction to give the phenol derivative represented by the general formula (I). On the other hand, as seen from Scheme 2, the compound represented by the general formula (I) wherein $R^4$ is unsubstituted can also be obtained by reducing the compound wherein $R^4$ is a halogen atom (chlorine or bromine). In Scheme 2, E is

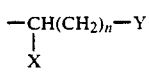

(wherein X, Y and n are as defined above); $R^{13}$ is hydrogen atom, a lower alkyl group having 1 to 6 carbon atoms, an aryl group or an aralkyl group; $R^{14}$ is a lower alkyl group having 1 to 6 carbon atoms or an aryl group; and $R^{15}$ is a lower alkyl group having 1 to 6 carbon atoms, an aryl group or aralkyl group.

Among the phenol derivatives represented by the general formula (I) of the present invention, those like in an in vitro experimental system. Further, in an in vivo experimental system, even if Y is methyl group, hydroxymethyl group, a substituted hydroxymethyl group, an esterified or amidated carboxyl group or cyano group, in the case that they are converted into carboxyl group by oxidation in the living body (e.g., $\omega$-oxidation, $\beta$-oxidation), such phenol derivative exert antagonistic activites to the receptor of eicosanoids such as thromboxane $A_2$, prostaglandin $H_2$, prostaglandin $D_2$ and the like.

In the living body, thromboxane $A_2$ is mainly biosynthesized from arachidonic acid in platelets or leukocytes through prostaglandin $H_2$. Physioligical activites of thromboxane $A_2$ and prostaglandin $H_2$ are to exert strong platelet aggregation activity and constriction activity against a blood vessel and bronchial smooth muscle in a very low concentration. For example, it has been well known that production of thromboxane $A_2$ is generally exasperated in patients with thrombosis, myocardial infarction, cerebral infarction, arterial sclerosis, diabetic hypertension, asthma and the like. Accordingly, it is considered that a compound having antagnostic activity to the receptor of thromboxane $A_2$ or prostaglandin $H_2$ can be used as an anti-thrombus agent, anti-vasoconstriction and vasospasm agent, antihypertensive, antiasthmatic or anti-arterial sclerosis agent for treating and preventing various diseases manifested by vasoconstriction, vasospasm, platelet aggregation, thrombus, airway constriction and the like.

Thus, the phenol derivatives of the general formula (I) of the present invention inhibit platelet aggregation caused by arachidonic acid, collagen, adenosine diphosphoric acid (ADP), platelet activating factor (PAF) and also inhibit pharmacological activities of U-44069 or U-46619 which is a prostaglandin $H_2$ analogue known as a substance for causing platelet aggregation, airway constriction and vasoconstriction through the receptor of thromboxane $A_2$ or prostaglantin $H_2$. Further, they exert improvement of manifestation of arrhythmia and an infraction site in a rat cardiac ischemia-refusion model and the like. Furthermore, they exert improvement of the function of rat ischemic kidney and improvement of cerebral ischemia stroke of spontaneous hypertensive rat.

Toxicity of the derivatives of the present invention is low and they can be safely administered orally or parenterally as they are or as phamaceutical compositions of known forms obtained by admixing them with known pharmaceutically acceptable carriers, excipients and the like, for example, tablets, capsules (including soft capsules and micro-capsules), liquids, injection preparations, suppositories and the like, according to pharmaceutically acceptable methods. The dosage is varied according to patients, routes of administration, conditions of dieseease to be treated and the like. However, in the case of oral administration to, for example, an adult patient, usually, a dose per one administration is about 0.1 to 20 mg/kg of body weight, preferably, about 0.1 to 10 mg/kg of body weight and, conveniently, the administration is carried out one to two times per day.

The phenol derivative represented by the general formula (I) of the present invention has a bulky group on the carbon atom at alpha ($\alpha$) position of the phenol side chain and has an asymmetric center. Usually, either of the optical isomers due to this asymmetric center has specifically strong antagonistic activity to the receptor of eicosanoides such as thrmoboxane $A_2$, prostaglandin $H_2$, prostaglandin $D_2$ and the like. Since the optical isomer which does not show the antagonistic activity to the receptor does not have any activity similar to that of thromboxane $A_2$, prostaglandin $H_2$, prostaglandin $D_2$ and the like, even the racemic compound thereof has no problem from the viewpoint of the pharmacological activity.

Further, since the compound of the present invention has the bulky group on the carbon atom of the alpha postion of the side chain, it is hardly inactivated by metabolism in the living body. Thereby, it can maintain the effective blood concentration of the drug for a long period of time and exert superior pharmacological activity with a low dosage.

The present invention is further illustrated in detail by the following Reference Examples for illustrating the preparation of the starting mateirals, Examples for illustrating the preparation of the phenol derivatives represented by the general formula (I) of the present invention, and Experiments for illustrating the pharmacological acitivties of the derivatives (I).

REFERENCE EXAMPLE 1

Preparation of Compounds A-1 to A-4

To a solution of 4-bromo-2,3,5-trimethylanisole (4.0 g) in anhydrous tetrahydrofuran were added 1.6M n-butyl lithium-hexane solution (12 ml) and then a solution of benzaldehyde (2.04 g) in tetrahydrofuran (10 ml) at $-78°$ C. The temperature was raised slowly to room temperature. An aqueous potassium hydrogen sulfate solution was added and the mixture was extracted with ethyl acetate. The organic layer was washed with water and saturated saline and dried with anhydrous magnesium sulfate, and the solvent was distilled off under reduced pressure to obtain $\alpha$-(4-methoxy-2,3,6-trimethylpehnyl)benzylalcohol (4.4 g) (Compound A-1). The physical properties and NMR spectrum data thereof are shown in Table 1.

Likewise, Compounds A-2 to A-4 as shown in Table 1 were prepared.

REFERENCE EXAMPLE 2

Preparation of Compounds A-5 to A-8

To a solution of 4,7-dimethyl-5-methoxyindane (3.5 g) in dichloromethane (30 ml) was added a solution of boron tribromide (5.08 g) in dichloromethane (2 ml) at $-78°$ C. The temperature was raised slowly to room temperature and the mixture was stirred at the same temperature for 1 hour. The mixture was extracted by addition of ice-water (10 ml) and ethyl acetate (50 ml). The organic layer was washed with aqueous sodium bicarbonate, water and saturated saline and dried with anhydrous magnesium sulfate, and the solvent was distilled off under reduced pressure. The residue was recrystallized from hexane to obtain 4,7-dimethyl-5-hydorxyindane (3.2 g) (Compound A-5). The physical properties and NMR spectrum data thereof are shown in Table 1.

Likewise, Compounds A-6 to A-8 as shown in Table 1 were prepared.

REFERENCE EXAMPLE 3

Preparation of Compounds A-9 to A-13

To a solution of 4,7-dimethyl-6-methoxy-1-indanol (4.0 g) in acetic acid (100 ml) was added palladium black (600 mg) and hydrogenation was carried out at room temperature for 3 hours. The catalyst was filtered off and the mother liquor was distilled under reduced pressure. To the residue was added ethyl acetate, washed with water and saturated saline and dried with anhydrous magnesium sulfate and the solvent was distilled off under reduced pressure to obtain 4,7-dimethyl-5-methoxyindane (3.5 g) (Compound A-9). The physical properties and NMR spectrum data thereof are shown in Table 1.

Likewise, Compounds A-10 to 13 as shown in Table 1 were prepared.

REFERENCE EXAMPLE 4

Preparation of Compounds A-14 to A-16

To a solution of 4,7-dimethyl-6-methoxy-1-indanone (7.0 g) in a mixed solvent of methanol (100 ml) and tetrahydrofuran (50 ml) was added sodium borohydride (1.2 g) at 0° C. and then the mixture was stirred at room temperature for 1 hour. Acetone (10 ml) was added and the solvent was distilled off under reduced pressure. Water (50 ml) and ethyl acetate (50 ml) were added and the organic layer was washed with water and saturated saline. The organic layer was dried with anhydrous magnesium sulfate and the solvent was removed under reduced pressure to obtain 4,7-dimethyl-6-methoxy-1-indanol (7.0 g) (Compound A-14). The physical properties and NMR spectrum data thereof are shown in Table 1.

Likewise, Compounds A-15 and A-16 as shown in Table 1 were prepared.

REFERENCE EXAMPLE 5

Preparation of Compounds A-17 to A-20

To 4-ethyl-2,3,5-trimethylanisole (7.8 g) was added 47% aqueous hydrogen bromide solution and the mixture was refluxed for 17 hours. Water was added to the solution and the mixture was extracted with ethyl acetate. The organic layer was washed with aqueous sodium hydrogen carbonate, water and saturated saline and dried with anhydrous magnesium sulfate. The solvent was distilled off under reduced pressure and the residue was recrystallized from hexane to obtain 4-ethyl-2,3,5-trimethylphenol (3.6 g) (Compound A-17). The physical properties and NMR spectrum data thereof are shown in Table 1.

Likewise, Compounds A-18 to A-20 as shown in Table 1 were prepared.

REFERENCE EXAMPLE 6

Preparation of Compound A-21

To a solution of 1,4-dimethoxy-2,5-dimethyl-3-chloromethylbenzene (2.5 g) in dimethylsulfoxide (8 ml) was added sodium cyanide (0.7 g) and the mixture was stirred at 60° C. for 3 hours. The reaction mixture was poured into water and extracted with ethyl acetate. The organic layer was washed with water and saturated saline and dried with anhydrous magnesium sulfate. The solvent was distilled off under reduced pressure to obtain and the residue was subjected to silica gel column chromatography to obtain 1,4-dimethoxy-2,5-dimethylphenylacetonitrile (1.4 g) (Compound A-21). The physical properties and NMR spectrum data thereof are shown in Table 1.

REFERENCE EXAMPLE 7

Preparation of Compound A-22

A mixture of 2,5-dimethoxy-3,6-dimethylbenzaldehyde (5.0 g), malonic acid (3.8 g), pyridine (6 ml) and piperidine (0.3 ml) was refluxed for 25 hours. The reaction mixture was poured into water and extracted with ethyl acetate. The organic layer was washed with 1N hydrochloric acid, water and saturated saline and dried with anhydrous magnesium sulfate. The solvent was distilled off under reduced pressure and recrystallized from ethanol to obtain 2,5-dimethoxy-3,6-dimethylcinnamic acid (4.1 g) (Compound A-22). The physical properties and NMR spectrum data thereof are shown in Table 1.

REFERENCE EXAMPLE 8

Preparation of Compound A-23

To a solution of 2,5-dimethoxy-3,6-dimethylcinnamic acid (2.0 g) in ethanol (30 ml) was added 5% palladium-carbon (0.2 g) and hydrogenation was carried out at room temperature. The catalyst was filtered off and washed with ethanol. The washing was combined with the filtrate and the mixture was concentrated to obtain almost purified 2,5-dimethoxy-3,6-dimethylpropionic acid (2.0 g) (Compound A-23). The physical properties and NMR spectrum data thereof are shown in Table 1.

REFERENCE EXAMPLE 9

Preparation of Compound A-24

To a solution of 4-hydroxy-2,3,6-trimethylphenylacetic acid (2.5 g) in anhydrous tetrahydrofuran (20 ml) was added lithium aluminum hydride (0.5 g) at 0° C. and the mixture was heated at 40° C. for 3 hours. The mixture was cooled to 0° C. Diluted sulfuric acid was added and the mixture was extracted with ethyl acetate. The organic layer was washed with water and saturated saline and dried with anhydrous magnesium sulfate and the solvent was distilled off under reduced pressure to obtain 2-(4-hydroxy-2,3,6-trimethylphenyl)ethanol (2.3 g) (Compound A-24). The physical properties and NMR spectrum data thereof are shown in Table 1.

REFERENCE EXAMPLE 10

Preparation of Compounds B-1 and B-2

According to the same manner as described in Example 1 hereinafter, 7-(4-fluorophenyl)-7-(2-hydroxy-3,4,6-trimethylphenyl)heptanoic acid (1.2 g) (Compound B-1) was prepared from 2,3,5-trimethylphenol (0.7 g) and 7-(4-fluorophenyl)-7-hydorxyheptanoic acid (1.3 g). The physical properties and NMR spectrum data thereof are shown in Table 2.

Likewise, Compound B-2 was prepared.

REFERENCE EXAMPLE 11

Preparation of Compound B-3

To a solution of 7-(4-bromo-1-hydroxy-2-naphthyl)-7-(4-fluorophenyl)heptanoic acid (1.70 g) in methanol (10 ml) were added 5% palladium-carbon (200 mg) and triethylamine (0.53 ml) and hydrogenation was carried out at room temperature for 1.5 hours. The catalyst was filtered off and the filtrate was distilled off at reduced pressure. The residue was extracted by addition of ethyl acetate and water. The ethyl acetate layer was washed with saturated saline and dried with anhydrous magnesium sulfate, and the solvent was distilled off under reduced pressure. The residue was purified by subjecting it to silica gel chromatography and eluting with ethyl acetate/hexane (1:2) to obtain 7-(4-fluorophenyl)-7-(1-hydroxy-2-naphthyl)heptanoic acid (930 mg) (Compound B-3). The physical properties and NMR spectrum data thereof are shown in Table 2.

REFERENCE EXAMPLE 12

Preparation of Compound B-4

A solution of 7-(4-fluorophenyl)-7-(2-hydroxy-3,4,6-trimethylphenyl)heptanoic acid (500 mg) in dimethylformamide (1 ml) was added to a dispersion of sodium hydride (67 mg) in dimethylformamide (4 ml) at 0° C. The mixture was stirred at room temperature for 30 minutes and methyl iodide (430 mg) was added dropwise. The mixture was stirred at the same temperature for 1 hour. Water (20 ml) was added and the mixture was extracted with ethyl acetate. The organic layer was washed with water and saturated saline and dried with anhydrous magnesium sulfate. The solvent was distilled off under reduced pressure to obtain methyl 7-(4-fluorophenyl)-7-(2-methoxy-3,4,6-trimethylphenyl)heptanoate (530 mg) (Compound B-4). The physical properties and NMR spectrum data thereof are shown in Table 2.

TABLE 1

[Structure: benzene ring with R⁴ (top), R³ (upper-left), R⁵ (upper-right), Me (left), R¹ (bottom)]

| Comp. No. | R¹ | R³ | R⁴ | R⁵ | Molecular formula Physical property m.p. (°C.) | NMR TMS Internal Standard δ (ppm) |
|---|---|---|---|---|---|---|
| A-1 | OMe | Me | —CHOH—Ph | Me | $C_{17}H_{20}O_2$ oil | 2.09(6H), 2.25(1H), 2.30(3H), 3.79(3H), 6.31(1H), 6.55(1H), 7.13–7.46(5H) |
| A-2 | —OCH₂—Ph | Me | —CHOH—(4-F-C₆H₄) | Me | $C_{23}H_{23}FO_2$ oil | 2.08(3H), 2.16(3H), 2.20(1H), 2.27(3H), 5.04(2H), 6.27(1H), 6.62(1H), 6.83–7.57(9H) |
| A-3 | OMe | Me | Et | Me | $C_{12}H_{18}O$ oil | 1.06(3H), 2.13(3H), 2.21(3H), 2.30(3H), 2.62(2H), 3.77(3H), 6.52(1H) |
| A-4 | OMe | Me | Hex | Me | $C_{16}H_{26}O$ oil | 0.88(3H), 1.12–1.65(8H), 2.13(3H), 2.20(3H), 2.30(3H), 2.67(2H), 3.77(3H), 6.54(1H) |
| A-5 | OH |  | —(CH₂)₃— | Me | $C_{11}H_{14}O$ 112.0–112.5 | 1.80–2.40(2H), 2.13(3H), 2.16(3H), 2.63–2.96(4H), 4.50(1H), 6.52(1H) |
| A-6 | OH | Me | —CH₂—Ph | Me | $C_{16}H_{18}O$ oil | 2.10(3H), 2.15(6H), 3.98(2H), 5.15(1H), 6.50(1H), 6.92–7.45(5H) |
| A-7 | OH | Me | —(CH₂)₃— |  | $C_{11}H_{14}O$ 123.0–124.0 | 1.60–2.30(2H), 2.11(3H), 2.15(3H), 2.64–2.96(4H), 4.54(1H), 6.50(1H) |
| A-8 | OH | Me | —(CH₂)₄— |  | $C_{12}H_{16}O$ 104.5–105.5 | 1.50–1.96(4H), 2.11(3H), 2.14(3H), 2.36–2.87(4H), 4.45(1H), 6.36(1H) |
| A-9 | OMe |  | —(CH₂)₃— | Me | $C_{12}H_{16}O$ 94.0–95.0 | 1.71–2.36(2H), 2.07(3H), 2.19(3H), 2.65–2.96(4H), 3.73(3H), 3.45(1H) |
| A-10 | OMe | Me | —CH₂—Ph | Me | $C_{17}H_{20}O$ 63.0–65.0 | 2.10(3H), 2.15(3H), 2.23(3H), 3.79(3H), 4.01(2H), 6.59(1H), 6.90–7.38(5H) |
| A-11 | OMe | Me | —(CH₂)₃— |  | $C_{12}H_{16}O$ 32.0–34.0 | 1.65–2.30(2H), 2.08(6H), 2.68–3.95(4H), 3.62(3H), 6.50(1H) |

TABLE 1-continued $$\begin{array}{c} R^4 \\ R^3 \diagup\!\!\!\diagdown R^5 \\ Me \diagdown\!\!\!\diagup \\ R^1 \end{array}$$

| Comp. No. | $R^1$ | $R^3$ | $R^4$ | $R^5$ | Molecular formula Physical property m.p. (°C.) | NMR TMS Internal Standard δ (ppm) |
|---|---|---|---|---|---|---|
| A-12 | OH | Me | F—C₆H₄—CH₂— (4-fluorobenzyl) | Me | $C_{16}H_{17}FO$ oil | 2.08(3H), 2.14(6H), 3.94(2H), 4.78(1H), 6.50(1H), 6.83-7.00(4H) |
| A-13 | OMe | Me | —(CH₂)₄— | | $C_{13}H_{18}O$ 60.5-61.5 | 1.55-2.00(4H), 2.14(3H), 2.16(3H), 2.48-2.87(4H), 3.78(3H), 6.47(1H) |
| A-14 | OMe | —CH(OH)—(CH₂)₂— | | Me | $C_{12}H_{16}O_2$ 193.0-195.0 | 1.55(1H), 1.86-3.30(4H), 2.23(6H), 3.78(3H), 5.29(1H), 6.60(1H) |
| A-15 | OMe | Me | —(CH₂)₂—CH(OH)— | | $C_{12}H_{16}O_2$ 91.0-92.0 | 1.60-3.19(4H), 1.72(1H), 2.14(3H), 2.17(3H), 3.81(3H), 5.19(1H), 6.80(1H) |
| A-16 | OMe | Me | —(CH₂)₃—CH(OH)— | | $C_{13}H_{18}O_2$ 75.0-75.5 | 1.60-2.10(5H), 2.13(3H), 2.16(3H) 2.45-2.73(2H), 3.82(3H), 4.60-4.88(1H), 6.86(1H) |
| A-17 | OH | Me | Et | Me | $C_{11}H_{16}O$ 57.0-57.5 | 1.05(3H), 2.13(3H), 2.21(6H), 2.60(2H), 4.73(1H), 6.42(1H) |
| A-18 | OH | Me | Hex | Me | $C_{15}H_{24}O$ 81.0-82.0 | 0.89(3H), 1.10-1.60(8H), 2.12(3H), 2.19(3H), 2.21(3H), 2.52(2H), 4.52(1H), 6.44(1H) |
| A-19 | OH | —CH₂—C(=O)—O— | | Me | $C_{10}H_{10}O_3$ 190° C. (dec.) | 2.06(3H), 2.17(3H), 3.68(2H), 6.55(1H), 8.51(1H) |
| A-20 | OH | —(CH₂)₂—C(=O)—O— | | Me | $C_{11}H_{12}O_3$ 165.0-170.0 | 2.14(3H), 2.20(3H), 2.45-3.05(4H), 5.04(1H), 6.55(1H) |
| A-21 | OMe | CH₂CN | OMe | Me | $C_{12}H_{15}NO_2$ 79.5-80.0 | 2.22(3H), 2.30(3H), 3.71(2H) 3.76(3H), 3.80(3H), 6.66(1H) |
| A-22 | OMe | —CH=CH—CH(COOH)— (with COOH branch) | OMe | Me | $C_{13}H_{16}O_4$ 167.0-168.0 | 2.23(3H), 2.27(3H), 3.60(3H), 3.79(3H), 6.55(1H), 6.68(1H), 7.96(1H), 9.52(1H), |
| A-23 | OMe | —CH₂—CH₂—CH(COOH)— | OMe | Me | $C_{13}H_{18}O_4$ 95.0-96.0 | 2.16(3H), 2.27(3H), 2.35-2.74(2H), 2.78-3.15(2H), 3.70(3H), 3.76(3H), 6.55(1H), 7.48(1H) |
| A-24 | OH | Me | —(CH₂)₂—OH | Me | $C_{11}H_{16}O_2$ 132.0-133.0 | 2.0(1H), 2.13(3H), 2.23(6H), 2.90(2H), 3.70(2H), 4.6(1H), 6.47(1H) |

TABLE 2

[Structure: benzene ring with substituents R³, R⁴, R⁵ (top), R², R¹ (side), bearing a CH linked to a (CH₂)₅COOR⁷ chain and a 4-fluorophenyl group]

| Comp. No. | R² | R³ | R⁴ | R⁵ | R¹ | R⁷ | Molecular formula Physical property m.p. (°C.) | NMR TMS Internal Standard δ (ppm) |
|---|---|---|---|---|---|---|---|---|
| B-1 | Me | Me | H | Me | OH | H | $C_{22}H_{27}FO_3$ 128.0–129.0 | 1.00–1.90(6H), 1.92–2.55(4H), 2.04(3H), 2.21(3H), 2.31(3H), 4.33(1H), 6.0–9.5(2H), 6.62(1H), 6.84–7.45(4H) |
| B-2 | Me | Me | H | Me | OH | Et | $C_{24}H_{31}FO_3$ oil | 1.00–1.83(6H), 1.21(3H), 1.86–2.52(4H), 2.03(3H), 2.21(3H), 2.30(3H), 4.08(2H), 4.32(1H), 4.48(1H), 6.60(1H), 6.83–7.42(4H) |
| B-3 | —(CH=CH)₂— | | H | H | OH | H | $C_{23}H_{23}FO_3$ 47.0–49.0 | 1.00–1.78(6H), 1.78–2.50(4H), 4.32(1H), 6.73–7.58(8H), 7.60–7.85(1H), 7.90–8.13(1H), 8.36(2H) |
| B-4 | Me | Me | H | Me | OMe | Me | $C_{24}H_{31}FO_3$ oil | 1.00–1.77(6H), 1.85–2.50(4H), 2.11(6H), 2.17(3H), 3.23(3H), 3.61(3H), 4.42(1H), 6.70(1H), 6.75–7.33(4H) |

EXAMPLE 1

Preparation of Compound 1

To a solution of 2,4,5-trimethylphenol (2.0 mg) and 7-(4-fluorophenyl)-7-hydroxyheptanoic acid (3.5 g) in toluene (60 ml) was added boron trifluoride ethyl ether (0.56 ml) at 70° C. and the reaction was carried out at the same temperature for 6 hours. After cooling in air, the reaction mixture was extracted by addition of water and ethyl acetate. The organic layer was washed in turn with water and saturated saline and dried with anhydrous magnesium sulfate, and the solvent was distilled off under reduced pressure. The residue was subjected to silica gel column chromatography and eluted with ethyl acetate/hexane (1 : 5) and the objective compound was recrystallized from ethyl acetate/hexane to obtain 7-(4-fluorophenyl)-7-(2-hydroxy-3,5,6-trimethylphenyl)heptanoic acid (4.5 g) (Compound 1). The physical properties and spectrum data thereof are shown in Tables 3 and 4.

Likewise, Compounds 2 to 4, 6, 8 to 11, 14 to 16, 19 to 26 and 44 to 46 were prepared.

EXAMPLE 2

Preparation of Compound 57

To a solution of 4,5-dimethylcatechol (663 mg) and 7-(4-fluorophenyl)-7-hydroxyheptanoic acid (1.15 g) in toluene (18 ml) was added sodium p-toluene sulfonate monohydrate (455 ml) and the reaction was carried out at 100° C. for 20 hours. After cooling in air, the reaction mixture was extracted by addition of water and ethyl acetate. The organic layer was separated, washed in turn with water and saturated saline and dried with anhydrous magnesium sulfate, and the solvent was distilled off under reduced pressure. The residue was purified by subjecting it to silica gel column chromatography and eluting with ethyl acetate/hexane (1:7) to obtain 7-(4-fluorophenyl)-7-(2,3-dihydroxy-5,6-dimethylphenyl)heptanoic acid (530 mg) (Compound 57). The physical properties and spectrum data thereof are shown in Tables 3 and 4.

Likewise, Compounds 54 to 56 were prepared.

EXAMPLE 3

Preparation of Compound 5

To a solution of ethyl 7-(2-hydroxy-3,5,6-trimethylphenyl)-7-phenylheptanoate (1.12 g) in tetrahydrofuran (20 ml) was added lithium aluminum hydride (0.17 g) with ice cooling and the mixture was stirred at room temperature for 3 hours. Diluted sulfuric acid was added to the reaction mixture and it was extracted with ethyl acetate. The organic layer was separated, washed in turn with water and saturated saline and dried with anhydrous magnesium sulfate, and the solvent was distilled off under reduced pressure. The residue was purified by subjecting it to silica gel column chromatography and eluting with ethyl acetate/hexane (1:4) to obtain 7-(2-hydroxy-3,5,6-trimethylphenyl)-7-phenylheptanol (0.81 g) (Compound 5). The physical properties and spectrum data thereof are shown in Tables 3 and 4.

EXAMPLE 4

Preparation of Compound 7

To a mixture of dichloromethane (10 ml) and dimethylformamide (0.43 ml) was added thionyl chloride (0.24 ml) at −10° C. and the mixture was stirred at the same temperature for 20 minutes. To this solution was added a solution of 7-(4-fluorophenyl)-7-(2-hydroxy-3,5,6-trimethylphenyl)heptanoic acid (1.0 g) in dichloromethane (5 ml) and the mixture was stirred at the same temperature for 1 hour. Isopropylamine (0.48 ml) and triethylamine (1.1 ml) were added and the temperature was raised slowly to room temperature. The reaction mixture was stirred at room temperature for 1 hour and washed in turn with 1N hydrochloric acid, water, aqueous sodium hydrogen carbonate, water and saturated saline and dried with anhydrous magnesium sulfate and the solvent was distilled off under reduced pressure. The residue was subjected to silica gel column chromatography and the resulting crystals were recrystallized from isopropyl ether to obtain N-isopropyl-7-(4-fluorophenyl)-7-(2-hydroxy-3,5,6-trimethylphenyl)heptane amide (0.64 g) (Compound 7). The physical properties and spectrum data thereof are shown in Tables 3 and 4.

EXAMPLE 5

Preparation of Compound 12

To a solution of 7-(4-fluorophenyl)-7-(2-hydroxy-3,4,6-trimethylphenyl)heptanoic acid (1.32 g) in acetic acid (10 ml) was added dropwise a solution of bromine (0.19 ml) in acetic acid (2 ml) with ice cooling. After completion of addition, the mixture was stirred at room temperature for 30 minutes. The reaction mixture was extracted by addition of water and ethyl acetate. The organic layer was separated and washed in turn with water and saturated saline and dried with anhydrous magnesium sulfate and the solvent was distilled off under reduced pressure. The residue was recrystallized from ethyl acetate/hexane to obtain 7-(5-bromo-2-hydroxy-3,4,6-trimethylphenyl)-7-(4-fluorophenyl)heptanoic acid (1.04 g) (Compound 12). The physical properties and spectrum data thereof are shown in Tables 3 and 4.

Likewise, Compound 13 was prepared.

EXAMPLE 6

Preparation of Compound 41

To a solution of ethyl 7-(4-fluorophenyl)-7-[2-hydroxy-5-(3-oxobutenyl)-3,4,6-trimethylphenyl]heptanoate (0.95 g) in tetrahydrofuran (15 ml) was added aqueous 1N sodium hydroxide (5 ml) and the mixture was stirred at room temperature for 15 hours. The solvent was distilled off under reduced pressure and the residue was acidified by addition of 1N hydrochloric acid and extracted with ethyl acetate. The organic layer was washed in turn with water and saturated saline and dried with anhydrous magnesium sulfate, and the solvent was distilled off under reduced pressure. The residue was recrystallized from acetonitrile to obtain 7-(4-fluorophenyl)-7-[2-hydroxy-5-(3-oxobutenyl)-3,4,6-trimethylphenyl]heptanoic acid (0.85 g) (Compound 41). The physical properties and spectrum data thereof are shown in Tables 3 and 4.

Likewise, Compounds 17, 29 and 33 were prepared.

EXAMPLE 7

Preparation of Compound 35

A solution of methyl 7-(3-acetyl-6-methoxy-2,4,5-trimethylphenyl)-7-(4-fluorophenyl)-7-hydroxyheptanoate (1.6 g) in dichloromethane (15 ml) was added dropwise to a solution of boron tribromide (1.4 ml) in dichloromethane (15 ml) at −78° C. The temperature was raised slowly to room temperature and the mixture was stirred for 5 hours. The reaction mixture was ice-cooled and water was added. The aqueous layer was extracted with ethyl acetate. The organic layer was washed with water and saturated saline and dried with anhydrous magnesium sulfate and the solvent was distilled off under reduced pressure. The residue was recrystallized from ethyl acetate/hexane to obtain 7-(3-acetyl-6-hydroxy-2,4,5-trimethylphenyl)-7-(4-fluorophenyl)heptanoic acid (0.87 g) (Compound 35). The physical properties and spectrum data thereof are shown in Tables 3 and 4.

Likewise, Compounds 40 and 43 were prepared.

EXAMPLE 8

Preparation of Compound 32

To a solution of 7-(4-fluorophenyl)-7-(3-formyl-6-hydroxy-2,4,5-trimethylphenyl)heptanoic acid (1.8 g) in tetrahydrofuran (30 ml) was added sodium borohydride (176 mg) at 0° C. and the mixture was stirred at room temperature for 2 hours. Acetone was added and the solvent was distilled off under reduced pressure. Water and ethyl acetate were added and the organic layer was separated. The organic layer was washed with water and saturated saline and dried with anhydrous magnesium sulfate. The solvent was distilled off under reduced pressure to obtain crystals. They were recrystallized from acetonitrile to obtain 7-(4-fluorophenyl)-7-(6-hydroxy-3-hydroxymethyl-2,4,5-trimethylphenyl)heptanoic acid (740 mg) (Compound 32). The physical properties and spectrum data thereof are shown in Tables 3 and 4.

EXAMPLE 9

Preparation of Compound 18

To 7-(4-fluorophenyl)-7-(2-hydroxy-3,4,6-trimethylphenyl)heptanoate (1.0 g) was added sulfuryl chloride (0.38 g) at 0° C. and the mixture was stirred at room temperature for 1 hour. Ice-water was added to the reaction mixture and the mixture was extracted with ethyl acetate. The organic layer was washed in turn with aqueous sodium hydrogen carbonate, water and saturated saline and dried with anhydrous magnesium sulfate. The solvent was distilled off to obtain ethyl 7-(5-chloro-2-hydroxy-3,4,6-trimethylphenyl)-7-(4-fluorophenyl)heptanoate (4.5 g) (Compound 18). The physical properties and spectrum data thereof are shown in Tables 3 and 4.

EXAMPLE 10

Preparation of Compound 27

To a solution of 7-(4-fluorophenyl)-7-(2-hydroxy-3,4,6-trimethylphenyl)heptanoic acid (7.5 g) and dichloromethyl methyl ether (5.7 ml) in dichloromethane (80 ml) was added a solution of titanium tetrachloride (6.9 ml) in dichloromethane (40 ml) over about 2 hours with ice-sodium chloride cooling. The reaction mixture was added to ice-water and the mixture was stirred for 30 minutes. The mixture was extracted with ethyl acetate. The organic layer was washed with water and saturated saline and dried with anhydrous magnesium sulfate. The solvent was distilled off under reduced pressure and the resulting crystals were recrystallized from acetonitrile to obtain 7-(4-fluorophenyl)-7-(3-formyl-6-hydroxy-2,4,5-trimethylphenyl)heptanoic acid (7.8 g) (Compound 27). The physical properties and spectrum data thereof are shown in Tables 3 and 4.

Likewise, Compounds 28, 30, 31 and 61 were prepared.

EXAMPLE 11

Preparation of Compound 34

To a solution of 7-(4-fluorophenyl)-7-(2-hydroxy-5-hydroxymethyl-3,4,6-tirmethylphenyl)heptanoic acid (0.67 g) in methanol (20 ml) was added conc. sulfuric acid (0.09 ml) at 0° C. and the mixture was stirred at room temperature for 30 minutes. The mixture was neutralized with addition of aqueous sodium hydrogen carbonate and concentrated under reduced pressure. The residue was extracted with ethyl acetate and the organic layer was washed in turn with aqueous sodium hydrogen carbonate, water and saturated saline and dried with anhydrous magnesium sulfate and the solvent was distilled off under reduced pressure. The residue was subjected to silica gel column chromatography to obtain methyl 7-(4-fluorophenyl)-7-(2-hydroxy-5-methoxymethyl-3,4,6-trimethylphenyl)heptanoate (0.5 g) (Compound 34). The physical properties and spectrum data thereof are shown in Tables 3 and 4.

EXAMPLE 12

Preparation of Compound 36

A mixture of methyl 7-(fluorophenyl)-7-(2-methoxy-3,4,6-trimethyl-5-valerylphenyl)heptanoate (0.23 g), collidine (0.38 ml) and lithium iodide (0.2 g) was refluxed for 18 hours. After allowing to cool, the mixture was acidified with addition of 1N hydrochloric acid and extracted with ethyl acetate. The organic layer was washed in turn with 1N hydrochloric acid, water and saturated saline and dried with anhydrous magnesium sulfate and the solvent was distilled off under reduced pressure. The residue was subjected to silica gel column chromatography to obtain 7-(fluorophenyl)-7-(2-hydroxy-3,4,6-trimethyl-5-valerylphenyl)heptanoic acid (0.1 g) (Compound 36). The physical properties and spectrum data thereof are shown in Tables 3 and 4.

Likewise, Compound 39 was prepared.

EXAMPLE 13

Preparation of Compound 42

To acetic acid (0.14 ml) were added pyrrolidine (0.2 ml) and acetone (0.26 ml). To this solution was added ethyl 7-(4-fluorophenyl)-7-(3-formyl-6-hydroxy-2,4,5-trimethylphenyl)heptanoate (1.0 g) and the mixture was stirred for 6.5 hours. Water was added and the mixture was extracted with ethyl acetate. The organic layer was washed with water and saturated saline and dried with anhydrous magnesium sulfate. The solvent was distilled off under reduced pressure to obtain ethyl 7-(4-fluorophenyl)-7-[2-hydroxy-5-(3-oxobutenyl)-3,4,6-trimethylphenyl]heptanoate (0.95 g) (Compound 42). The physical properties and spectrum data thereof are shown in Tables 3 and 4.

EXAMPLE 14

Preparation of Compounds 47 and 48

To a solution 7-(4-fluorophenyl)-7-(3-formyl-6-hydroxy-2,4,5-trimethylphenyl)heptanoic acid (1.3 g) in ethanol (13 ml) were added sodium acetate (1.3 g), hydroxylamine hydrochloride (0.26 g) and water (2.6 ml) and the mixture was refluxed for 4 hours. The solvent was distilled off under reduced pressure. To the residue were added water and 1N hydrochloric acid and extracted with ethyl acetate. The organic layer was washed with water and saturated saline and dried with anhydrous magnesium sulfate. The solvent was distilled off under reduced pressure and the residue was subjected to silica gel column chromatography to obtain (Z)-7-(4-fluorophenyl)-7-(2-hydroxy-5-hydroxyiminomethyl-3,4,6-trimethylphenyl)heptanoic acid (0.55 g) and (E)-7-(4-fluorophenyl)-7-(2-hydroxy-5-hydroxyiminomethyl-3,4,6-trimethylphenyl)heptanoic acid (0.75 g) (Compounds 47 and 48). The physical properties and spectrum data thereof are shown in Tables 3 and 4.

Likewise, Compounds 49 to 53 were prepared.

EXAMPLE 15

Preparation of Compound 59

To a solution of methyl 7-(4-fluorophenyl)-7-(2-methoxy-3,4-dimethyl-5,6,7,8-tetrahydronaphthyl)heptanoate (0.4 g) in benzene (12 ml) was added a mixture of pyridinium chlorochromate (1 g) and cerite (1.8 g) and the mixture was refluxed for 5 hours. After cooling, insoluble materials were filtered off and the filtrate was washed with water and saturated saline and dried with anhydrous magnesium sulfate. The solvent was distilled off under reduced pressure and the residue was subjected to silica gel column chromatography to obtain methyl 7-(4-fluorophenyl)-7-(6-methoxy-7,8-dimethyl-1-oxo-1,2,3,4-tetrahydro-5naphthyl)-heptanoate (0.22 g) (Compound 59). The physical properties and spectrum data thereof are shown in Tables 3 and 4.

EXAMPLE 16

Preparation of Compound 58

A solution of methyl 7-(4-fluorophenyl)-7-(2-hydroxy-3,4-dimethyl-5,6,7,8-tetrahydronaphthyl)heptanoate (0.5 g) in dimethylformamide (1 ml) was added to a mixture of 60% sodium hydride (51 mg) and dimethylformamide (2 ml) at 0° C. The reaction mixture was stirred at room temperature for 30 minutes. Methyl iodide (82 ml) was added dropwise and the mixture was stirred at the same temperature for 2 hours. Water was added and the mixture was extracted with ethyl acetate. The organic layer was washed with water and saturated saline and dried with anhydrous magnesium sulfate. The solvent was distilled off under reduced pressure and the residue was subjected to silica gel column chromatography to obtain methyl 7-(4-fluorophenyl)-7-(2-methoxy-3,4-dimethyl-5,6,7,8-tetrahydronaphthyl)heptanoate (0.4 g) (Compound 58). The physical properties and spectrum data thereof are shown in Tables 3 and 4.

Likewise, Compound 60 was prepared.

EXAMPLE 17

Preparation of Compound 62

To a solution of methyl 7-(4-fluorophenyl)-7-(3-formyl-6-methoxy-2,4,5-trimethylphenyl)heptanoate (1.0 g) in anhydrous tetrahydrofuran was added dropwise a solution of methyl magnesium bromide in tetrahydrofuran at −78° C. until the starting material was disappeared. Aqueous potassium hydrogen sulfate was added and the mixture was extracted with ethyl acetate. The organic layer was washed with water and saturated saline and dried with anhydrous magnesium sulfate and the solvent was distilled off under reduced pressure. The residue was subjected to silica gel column chromatography to obtain methyl 7-(4-fluorophenyl)-7-[3-(1-hydroxyethyl)-6-methoxy-2,4,5-tirmethylphenyl)heptanoate (0.73 g) (Compound 62). The physical properties and spectrum data thereof are shown in Tables 3 and 4.

Likewise, Compound 63 was prepared.

EXAMPLE 18

Preparation of Compound 64

To a solution methyl 7-(4-fluorophenyl)-7-[3-(1-hydroxyethyl)-6-methoxy-2,4,5-trimethylphenyl]heptanoate (1.4 g) in benzene was added activated manganese dioxide (1.4 g) and the mixture was stirred for 1.5 hours. The catalyst was filtered off and washed with ethanol. The washing was combined with the filtrate and the mixture was concentrated to obtain methyl 7-(3-acetyl-6-methoxy-2,4,5-trimethylphenyl)-7-(fluorophenyl)hepanoate (1.3 g) (Compound 64). The physical properties and spectrum data thereof are shown in Tables 3 and 4.

Likewise, Compound 66 was prepared.

EXAMPLE 19

Preparation of Compound 65

To a solution methyl 7-(4-fluorophenyl)-7-(3-formyl-6-methoxy-2,4,5-trimethylphenyl)heptanoate (3.7 g) in anhydrous tetrahydrofuran (75 ml) was added 1.6 M solution of n-butyl lithium-hexane (6.2 ml) at −78° C. over 25 minutes. The mixture was stirred at the same temperature for 1 hour and aqueous potassium hydrogen sulfate was added. The mixture was extracted with ethyl acetate. The organic layer was washed with water and saturated saline and dried with anhydrous magnesium sulfate. The solvent was distilled off under reduced pressure and the residue was subjected to silica gel column chromatography to obtain methyl 7-(4-fluorophenyl)-7-[3-(1-hydroxypentyl)-6-methoxy-2,4,5-trimethylphenyl]heptanoate (2.8 g) (Compound 65). The physical properties and spectrum data thereof are shown in Tables 3 and 4.

EXAMPLE 20

Preparation of Compound 67

To a solution of methyl 7-(4-fluorophenyl)-7-(3-formyl-6-methoxy-2,4,5-trimethylphenyl)heptanoate (4.0 g) and butyl triphenylphosphonium bromide (4.6 g) in anhydrous tetrahydrofuran (40 ml) was added potassium t-butoxide (1.3 g) at 0° C. and the mixture was stirred at room temperature for 1 hour. Aqueous potassium hydrogen sulfate was added and the mixture was extracted with ethyl acetate. The organic layer was washed with water and saturated saline and dried with anhydrous magnesium sulfate. The solvent was distilled off under reduced pressure and the residue was subjected to silica gel column chromatography to obtain methyl 7-(4-fluorophenyl)-7-[2-methoxy-3,4,6-trimethyl-5-(1-pentenyl)phenyl]heptanoate (2.8 g) (Compound 67). The physical properties and spectrum data thereof are shown in Tables 3 and 4.

EXAMPLE 21

Preparation of Compound 37

To a solution of methyl 7-(6,7-dimethyl-5-hydroxyindan-4-yl)-7-(4-fluorophenyl)heptanoate (1.4 g) in benzene (40 ml) was added a mixture of pyridinium chlorochromate (3.8 g) and cerite (7 g) and the mixture was stirred for 2 hours. The reaction mixture was filtered and the filtrate was washed with water and saturated saline and dried with magnesium sulfate. Tetrahydrofuran (10 ml) and 1N sodium hydroxide (10 ml) were added to the residue and the mixture was stirred at room temperature for 13 hours. The solvent was distilled off under reduced pressure and the residue was acidified with hydrochloric acid and extracted with ethyl acetate. The organic layer was washed with water and saturated saline and dried with anhydrous magnesium sulfate. The solvent was distilled off under reduced pressure and the residue was recrystallized from acetonitrile to obtain 7-(6,7-dimethyl-5-hydroxy-1-oxoindan-4-yl)-7-(4-fluorophenyl)heptanoic acid (0.4 g) (Compound 37). The physical properties and spectrum data thereof are shown in Tables 3 and 4.

Likewise, Compound 38 was prepared.

EXAMPLE 22

Preparation of Compound 68

To a solution benzyl 7-(2-benzyloxy-5-formyl-3,4,6-trimethylphenyl)-7-(4-fluorophenyl)heptanoate (2.3 g) in dioxane (20 ml) and water (2 ml) was added silver oxide (II) (4.5 g) and the mixture was stirred for 12 days. Insoluble materials were filtered off and washed with ethyl acetate. The washing was combined with the filtrate and the mixture was concentrated. Ethyl acetate was added and the mixture was washed with water and saturated saline and dried with anhydrous magnesium sulfate. The solvent was distilled off under reduced pressure and the residue was subjected to silica gel column chromatography to obtain benzyl 7-(2-benzyloxy-5-carboxy-3,4,6-trimethylphenyl)-7-(4fluorophenyl)heptanoic acid (1.5 g) (Compound 68). The physical properties and spectrum data thereof are shown in Tables 3 and 4.

TABLE 3

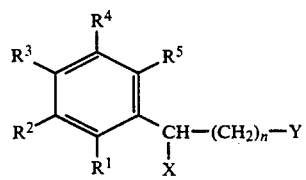

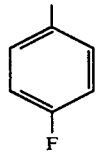

| Comp. No. | R¹ | R² | R³ | R⁴ | R⁵ | X | Y | n | Composition formula | m.p. (°C.) Physical property |
|---|---|---|---|---|---|---|---|---|---|---|
| 1 | OH | Me | H | Me | Me | | COOH | 5 | $C_{22}H_{27}FO_3$ | 142.0–143.0 |

TABLE 3-continued
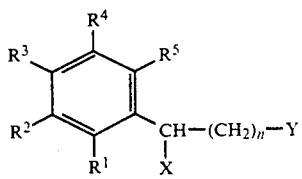
| Comp. No. | R¹ | R² | R³ | R⁴ | R⁵ | X | Y | n | Composition formula | m.p. (°C.) Physical property |
|---|---|---|---|---|---|---|---|---|---|---|
| 2 | OH | Me | H | Me | Me | 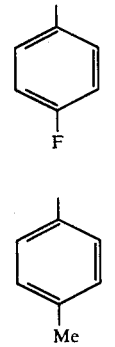 4-F-C₆H₄ | COOH | 7 | $C_{24}H_{31}FO_3$ | 128.0–129.0 |
| 3 | OH | Me | H | Me | Me | 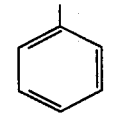 4-Me-C₆H₄ | COOH | 7 | $C_{25}H_{34}O_3$ | 125.0–126.0 |
| 4 | OH | Me | H | Me | Me | 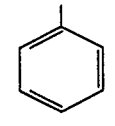 C₆H₅ | COOEt | 5 | $C_{24}H_{32}O_3$ | oil |
| 5 | OH | Me | H | Me | Me | 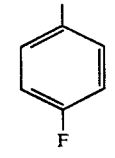 C₆H₅ | CH₂OH | 5 | $C_{22}H_{30}O_2$ | oil |
| 6 | OH | Me | H | Me | Me | 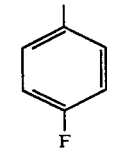 4-F-C₆H₄ | CH₃ | 5 | $C_{22}H_{29}FO$ | oil |
| 7 | OH | Me | H | Me | Me | 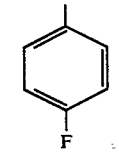 4-F-C₆H₄ | CONHisoPr | 5 | $C_{25}H_{34}FNO_2$ | 103.0–104.0 |
| 8 | OH | H | H | t-Bu | H | 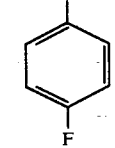 4-F-C₆H₄ | COOH | 5 | $C_{23}H_{29}FO_3$ | oil |
| 9 | OH | Me | Me | Me | Me | 4-F-C₆H₄ | COOH | 5 | $C_{23}H_{29}FO_3$ | 161.0–163.0 |

TABLE 3-continued

Structure: phenyl ring with R³, R⁴, R⁵ (top) and R², R¹ substituents, with side chain –CH(X)–(CH₂)ₙ–Y

| Comp. No. | R¹ | R² | R³ | R⁴ | R⁵ | X | Y | n | Composition formula | m.p. (°C.) Physical property |
|---|---|---|---|---|---|---|---|---|---|---|
| 10 | OH | Me | Me | Et | Me | 4-F-C₆H₄ | COOMe | 5 | $C_{25}H_{33}FO_3$ | oil |
| 11 | OH | Me | Me | Hex | Me | 4-F-C₆H₄ | COOMe | 5 | $C_{29}H_{41}FO_3$ | oil |
| 12 | OH | Me | Me | Br | Me | 4-F-C₆H₄ | COOH | 5 | $C_{22}H_{26}BrFO_3$ | 138.0–140.0 |
| 13 | OH | Me | Br | Me | Me | 4-F-C₆H₄ | COOH | 5 | $C_{22}H_{26}BrFO_3$ | 44.5–46.5 |
| 14 | OH | Me | H | Br | H | C₆H₅ | COOH | 5 | $C_{20}H_{23}BrO_3$ | oil |
| 15 | OH | –(CH=CH)₂– | | Br | H | C₆H₅ | COOH | 5 | $C_{23}H_{23}BrO_3$ | oil |
| 16 | OH | –(CH=CH)₂– | | Br | H | 4-F-C₆H₄ | COOH | 5 | $C_{23}H_{22}BrFO_3$ | oil |
| 17 | OH | Me | Me | Cl | Me | 4-F-C₆H₄ | COOH | 5 | $C_{22}H_{26}ClFO_3$ | 165.0–166.0 |

TABLE 3-continued structure: benzene ring with R³ (top-left), R⁴ (top), R⁵ (top-right), R² (bottom-left), R¹ (bottom), and substituent –CH(X)–(CH₂)ₙ–Y

| Comp. No. | R¹ | R² | R³ | R⁴ | R⁵ | X | Y | n | Composition formula | m.p. (°C.) Physical property |
|---|---|---|---|---|---|---|---|---|---|---|
| 18 | OH | Me | Me | Cl | Me | 4-F-C₆H₄– | COOEt | 5 | $C_{24}H_{30}ClFO_3$ | oil |
| 19 | OH | Me | Me | CH₂–C₆H₅ | Me | 4-F-C₆H₄– | COOH | 5 | $C_{29}H_{33}FO_3$ | 166.0–167.0 |
| 20 | OH | Me | Me | CH₂–(4-F-C₆H₄) | Me | 4-F-C₆H₄– | COOH | 5 | $C_{29}H_{32}F_2O_3$ | 151.0–152.0 |
| 21 | OH | Me | –(CH₂)₃– | | Me | 4-F-C₆H₄– | COOH | 5 | $C_{24}H_{29}FO_3$ | 164.0–164.5 |
| 22 | OH | Me | Me | –(CH₂)₃– | | 4-F-C₆H₄– | COOH | 5 | $C_{24}H_{29}FO_3$ | 166.5–167.0 |
| 23 | OH | Me | Me | –(CH₂)₃– | | 4-F-C₆H₄– | COOMe | 5 | $C_{25}H_{31}FO_3$ | 87.0–88.0 |
| 24 | OH | Me | –(CH₂)₃– | | Me | 4-F-C₆H₄– | COOMe | 5 | $C_{25}H_{31}FO_3$ | 115.0–115.5 |
| 25 | OH | t-Bu | H | –(CH₂)₃– | | 4-F-C₆H₄– | COOH | 5 | $C_{26}H_{33}FO_3$ | 140.0–141.0 |

TABLE 3-continued $$\text{structure as shown}$$

| Comp. No. | $R^1$ | $R^2$ | $R^3$ | $R^4$ | $R^5$ | X | Y | n | Composition formula | m.p. (°C.) Physical property |
|---|---|---|---|---|---|---|---|---|---|---|
| 26 | OH | Me | Me | —(CH$_2$)$_4$— | | 4-F-C$_6$H$_4$ | COOMe | 5 | C$_{26}$H$_{33}$FO$_3$ | oil |
| 27 | OH | Me | Me | CHO | Me | 4-F-C$_6$H$_4$ | COOH | 5 | C$_{23}$H$_{27}$FO$_4$ | 202.0–203.5 |
| 28 | OH | —(CH=CH)$_2$— | | CHO | H | 4-F-C$_6$H$_4$ | COOH | 5 | C$_{24}$H$_{23}$FO$_4$ | 166.0–167.0 |
| 29 | OH | Me | CHO | Me | Me | 4-F-C$_6$H$_4$ | COOH | 5 | C$_{23}$H$_{27}$FO$_4$ | 167.0–168.0 |
| 30 | OH | Me | Me | CHO | Me | 4-F-C$_6$H$_4$ | COOEt | 5 | C$_{25}$H$_{31}$FO$_4$ | 66.0–67.0 |
| 31 | OH | Me | CHO | Me | Me | 4-F-C$_6$H$_4$ | COOMe | 5 | C$_{24}$H$_{29}$FO$_4$ | oil |
| 32 | OH | Me | Me | CH$_2$OH | Me | 4-F-C$_6$H$_4$ | COOH | 5 | C$_{23}$H$_{29}$FO$_4$ | 184.0–185.0 |
| 33 | OH | Me | Me | CH$_2$OMe | Me | 4-F-C$_6$H$_4$ | COOH | 5 | C$_{24}$H$_{31}$FO$_4$ | 141.0–142.0 |

TABLE 3-continued

[Structure: benzene ring with substituents $R^1, R^2, R^3, R^4, R^5$ and a $CH(X)-(CH_2)_n-Y$ side chain]

| Comp. No. | $R^1$ | $R^2$ | $R^3$ | $R^4$ | $R^5$ | X | Y | n | Composition formula | m.p. (°C.) Physical property |
|---|---|---|---|---|---|---|---|---|---|---|
| 34 | OH | Me | Me | CH$_2$OMe | Me | 4-F-C$_6$H$_4$- | COOMe | 5 | C$_{25}$H$_{33}$FO$_4$ | oil |
| 35 | OH | Me | Me | C(O)Me | Me | 4-F-C$_6$H$_4$- | COOH | 5 | C$_{24}$H$_{29}$FO$_4$ | 163.5–164.5 |
| 36 | OH | Me | Me | O=C-(CH$_2$)$_3$-CHMe | Me | 4-F-C$_6$H$_4$- | COOH | 5 | C$_{27}$H$_{35}$FO$_4$ | 98.0–99.0 |
| 37 | OH | Me | Me | -C(O)-(CH$_2$)$_2$- | | 4-F-C$_6$H$_4$- | COOH | 5 | C$_{24}$H$_{27}$FO$_4$ | 225.0–226.0 |
| 38 | OH | Me | -(CH$_2$)$_2$-C(O)- | | Me | 4-F-C$_6$H$_4$- | COOH | 5 | C$_{24}$H$_{27}$FO$_4$ | 245.0–246.0 |
| 39 | OH | Me | Me | -C(O)-(CH$_2$)$_3$- | | 4-F-C$_6$H$_4$- | COOH | 5 | C$_{25}$H$_{29}$FO$_4$ | 160.0–161.0 |
| 40 | OH | Me | Me | (CH$_2$)$_2$-CH=CH-Me | Me | 4-F-C$_6$H$_4$- | COOH | 5 | C$_{27}$H$_{35}$FO$_3$ | oil |
| 41 | OH | Me | Me | O=C(Me)-CH=CH-Me | Me | 4-F-C$_6$H$_4$- | COOH | 5 | C$_{26}$H$_{31}$FO$_4$ | 144.0–145.0 |

TABLE 3-continued $$\begin{array}{c}\text{R}^3\text{-R}^4\text{-R}^5\text{-benzene-CH(X)-(CH}_2)_n\text{-Y, with R}^1, \text{R}^2\end{array}$$

| Comp. No. | $R^1$ | $R^2$ | $R^3$ | $R^4$ | $R^5$ | X | Y | n | Composition formula | m.p. (°C.) Physical property |
|---|---|---|---|---|---|---|---|---|---|---|
| 42 | OH | Me | Me | $\underset{\text{(CH=CH-C(O)Me)}}{\text{COMe via CH=CH}}$ | Me | 4-F-C$_6$H$_4$ | COOEt | 5 | $C_{28}H_{35}FO_4$ | oil |
| 43 | OH | Me | Me | COOH | Me | 4-F-C$_6$H$_4$ | COOH | 5 | $C_{23}H_{27}FO_5$ | 159.0–160.0 |
| 44 | OH | Me | Me | COOH–CH$_2$– | Me | 4-F-C$_6$H$_4$ | COOH | 5 | $C_{24}H_{29}FO_5$ | 153.0–153.5 |
| 45 | OH | Me | Me | OH–(CH$_2$)$_2$– | Me | 4-F-C$_6$H$_4$ | COOH | 5 | $C_{24}H_{31}FO_4$ | 144.0–145.0 |
| 46 | OH | —(CH=CH)$_2$— | | Me | H | 4-F-C$_6$H$_4$ | COOH | 5 | $C_{24}H_{25}FO_3$ | oil |
| 47 | OH | Me | Me | E isomer CH=N–OH | Me | 4-F-C$_6$H$_4$ | COOH | 5 | $C_{23}H_{28}FNO_4$ | 144.5–145.0 |
| 48 | OH | Me | Me | Z isomer CH=N–OH | Me | 4-F-C$_6$H$_4$ | COOH | 5 | $C_{23}H_{28}FNO_4$ | 133.0–134.0 |
| 49 | OH | Me | Me | E + Z isomers CH=N–OMe | Me | 4-F-C$_6$H$_4$ | COOH | 5 | $C_{24}H_{30}FNO_4$ | 146.0–150.0 |

TABLE 3-continued $$\underset{\substack{R^1 \\ R^2}}{\overset{\substack{R^4 \\ R^3}}{\bigcirc}} \underset{X}{\overset{R^5}{\text{CH}-(CH_2)_n-Y}}$$

| Comp. No. | $R^1$ | $R^2$ | $R^3$ | $R^4$ | $R^5$ | X | Y | n | Composition formula | m.p. (°C.) Physical property |
|---|---|---|---|---|---|---|---|---|---|---|
| 50 | OH | Me | Me | E + Z isomers $\underset{N}{\diagup}\overset{CEt}{\diagdown}$ | Me | 4-F-C$_6$H$_4$- | COOH | 5 | $C_{25}H_{32}FNO_4$ | 80.0–82.0 |
| 51 | OH | Me | Me | E + Z isomers $\underset{N}{\diagup}\overset{OBu}{\diagdown}$ | Me | 4-F-C$_6$H$_4$- | COOH | 5 | $C_{27}H_{36}FNO_4$ | 79.0–80.0 |
| 52 | OH | Me | Me | E + Z isomers $\underset{N}{\diagup}\overset{O\diagdown\text{allyl}}{\diagdown}$ | Me | 4-F-C$_6$H$_4$- | COOH | 5 | $C_{26}H_{32}FNO_4$ | 89.0–93.0 |
| 53 | OH | Me | Me | E + Z isomers $\underset{N}{\diagup}\overset{O-CHPh_2}{\diagdown}$ | Me | 4-F-C$_6$H$_4$- | COOH | 5 | $C_{36}H_{38}FNO_4$ | 113.0–116.0 |
| 54 | OH | Me |  | $-CH_2-\overset{O}{\overset{\|}{C}}-$ | Me | 4-F-C$_6$H$_4$- | COOH | 5 | $C_{23}H_{25}FO_5$ | 193.0–194.0 |
| 55 | OH | Me |  | $-(CH_2)_2\overset{O}{\overset{\|}{C}}-$ | Me | 4-F-C$_6$H$_4$- | COOH | 5 | $C_{24}H_{27}FO_5$ | 162.0–163.0 |
| 56 | OH | OH | H | t-Bu | H | C$_6$H$_5$- | COOH | 5 | $C_{23}H_{30}O_4$ | oil |
| 57 | OH | OH | H | Me | Me | 4-F-C$_6$H$_4$- | COOH | 5 | $C_{21}H_{25}FO_4$ | 95.0–96.0 |

TABLE 3-continued

| Comp. No. | R¹ | R² | R³ | R⁴ | R⁵ | X | Y | n | Composition formula | m.p. (°C.) Physical property |
|---|---|---|---|---|---|---|---|---|---|---|
| 58 | OMe | Me | Me | —(CH$_2$)$_4$— | | 4-F-C$_6$H$_4$ | COOMe | 5 | C$_{27}$H$_{35}$FO$_3$ | oil |
| 59 | OMe | Me | Me | —C(O)—(CH$_2$)$_3$— | | 4-F-C$_6$H$_4$ | COOMe | 5 | C$_{27}$H$_{33}$FO$_4$ | oil |
| 60 | OMe | Me | Me | CHO | Me | 4-F-C$_6$H$_4$ | COOMe | 5 | C$_{25}$H$_{31}$FO$_4$ | oil |
| 61 | OBz | Me | Me | CHO | Me | 4-F-C$_6$H$_4$ | COOBz | 5 | C$_{37}$H$_{39}$FO$_4$ | oil |
| 62 | OMe | Me | Me | CH(OH)Me | Me | 4-F-C$_6$H$_4$ | COOMe | 5 | C$_{26}$H$_{35}$FO$_4$ | oil |
| 63 | OBz | Me | Me | CH(OH)Me | Me | 4-F-C$_6$H$_4$ | COOBz | 5 | C$_{38}$H$_{43}$FO$_4$ | oil |
| 64 | OMe | Me | Me | C(O)Me | Me | 4-F-C$_6$H$_4$ | COOMe | 5 | C$_{26}$H$_{33}$FO$_4$ | oil |
| 65 | OMe | Me | Me | C(Me)(OH)(CH$_2$)$_3$– | Me | 4-F-C$_6$H$_4$ | COOMe | 5 | C$_{30}$H$_{41}$FO$_4$ | oil |

TABLE 3-continued

Structure:

$R^3, R^4, R^5, R^2, R^1$ substituents on benzene ring with $-CH(X)-(CH_2)_n-Y$

| Comp. No. | $R^1$ | $R^2$ | $R^3$ | $R^4$ | $R^5$ | X | Y | n | Composition formula | m.p. (°C.) Physical property |
|---|---|---|---|---|---|---|---|---|---|---|
| 66 | OMe | Me | Me | Me, O=C-(CH$_2$)$_3$- | Me | 4-F-C$_6$H$_4$- | COOMe | 5 | $C_{30}H_{39}FO_4$ | oil |
| 67 | OMe | Me | Me | Me, -(CH$_2$)$_2$-CH=CH- | Me | 4-F-C$_6$H$_4$- | COOMe | 5 | $C_{29}H_{39}FO_3$ | oil |
| 68 | OBz | Me | Me | COOH | Me | 4-F-C$_6$H$_4$- | COOBz | 5 | $C_{37}H_{39}FO_3$ | oil |

TABLE 4

| Comp. No. | NMR TMS Internal Standard δ (ppm) |
|---|---|
| 1 | 0.90–1.80(6H), 1.82–2.50(4H), 2.12(3H), 2.22(6H), 4.50(1H), 6.75–7.50(6H), 8.90–9.90(1H) |
| 2 | 1.10–1.83(10H), 1.95–2.50(4H), 2.09 (3H), 2.19(6H), 4.48(1H), 3.5–8.5(2H), 6.76–7.38(4H), 6.80(1H) |
| 3 | 1.05–2.60(14H), 2.09(3H), 2.22(3H), 2.26(3H), 2.31(3H), 4.47(1H), 6.0–13.0(2H), 6.81(1H), 7.01–7.35(4H) |
| 4 | 1.10–1.90(6H), 1.22(3H), 2.00–2.60(4H), 2.17(6H), 2.22(3H), 4.11(2H), 4.53(1H), 6.56(1H), 6.86(1H), 7.08–7.43(5H) |
| 5 | 0.78–1.80(8H), 1.80–2.60(2H), 2.07(3H), 2.20(6H), 3.49(2H), 4.55(1H), 4.75(1H), 6.80(1H), 7.00–7.45(6H) |
| 6 | 1.83(3H), 1.05–1.50(8H), 1.88–2.50(2H), 1.88(3H), 2.16(6H), 4.30–4.70(2H), 6.65–7.36(5H) |
| 7 | 0.75–2.45(10H), 1.07(6H), 2.11(6H), 2.16(3H), 3.70–4.30(1H), 4.51(1H), 5.28(1H), 5.74(1H), 6.70–7.38(4H), 6.79(1H) |
| 8 | 1.10–1.80(6H), 1.27(9H), 1.86–2.17(2H), 2.30(2H), 4.20(1H), 5.5–9.3(2H), 6.63(1H), 6.81–7.36(6H) |
| 9 | 1.10–1.90(8H), 1.90–2.40(2H), 2.07(3H), 2.17(6H), 2.19(3H), 4.50(1H), 6.75–7.45(5H), 8.30–9.70(1H) |
| 10 | 0.95–1.80(6H), 1.07(3H), 1.85–2.40(4H), 2.05(3H), 2.18(3H), 2.23(3H) 2.66(2H), 3.60(3H), 4.36(1H), 4.48(1H), 6.83–7.35(4H) |
| 11 | 0.90(3H), 1.05–1.82(14H), 1.85–2.40(4H), 2.05(3H), 2.20(3H), 2.26(3H), 2.62(3H), 3.61(3H), 4.35(1H), 4.48(1H), 6.82–7.35(4H) |
| 12 | 1.13–1.82(6H), 1.82–2.55(4H), 2.12(3H), 2.39(3H), 2.47(3H) 4.52(1H), 6.80–7.40(6H) |
| 13 | 1.00–1.85(6H), 1.85–2.60(4H), 2.25(3H), 2.33(3H), 2.75(3H), 4.92(1H), 6.71–7.55(5H), 7.60(1H) |
| 14 | 1.03–1.78(6H), 1.80–2.55(4H), 2.10(3H), 4.10(1H), 7.02–7.40(7H), 8.07(2H) |
| 15 | 0.96–1.72(6H), 1.75–2.40(4H), 4.27(1H), 6.93–7.59(7H), 7.66(1H), 7.93–8.22(2H), 8.56(2H) |
| 16 | 1.13–1.82(6H), 1.92–2.48(4H), 4.28(1H), 6.40–7.80(2H), 6.84–7.60(6H), 7.61(1H), 7.93–8.24(2H) |
| 17 | 1.00–1.78(6H), 1.80–2.45(4H), 2.34(3H), 2.21(3H), 2.29(3H), 4.56(1H), 6.60–7.70(6H) |
| 18 | 1.00–1.80(6H), 1.20(3H), 1.82–2.50(4H), 2.09(3H), 2.32(3H), 2.40(3H), 2.09(2H), 4.48(1H), 4.51(1H), 6.84–7.40(4H) |
| 19 | 1.03–1.85(6H), 1.88–2.43(4H), 2.07(3H), 2.11(3H), 2.17(3H), 4.06(2H), 4.08(1H), 6.85–7.43(11H) |
| 20 | 1.00–1.82(6H), 1.90–2.50(4H), 2.31(6H), 2.16(3H), 4.03(2H), 4.50(1H), 6.84–7.47(9H), 6.50–9.20(1H) |
| 21 | 1.00–1.83(6H), 1.83–2.45(6H), 2.03(3H), 2.20(3H), 2.66–3.00(4H), 4.37(1H), 6.0–8.2(2H), 6.34–7.40(4H) |
| 22 | 1.00–2.42(12H), 2.06(3H), 2.14(3H), 2.65–3.06(4H), 4.21(1H), 6.50–7.50(6H) |
| 23 | 1.00–1.78(6H), 1.80–2.40(8H), 2.06(3H), 2.15(3H), 2.67–3.00(4H), 3.63(3H), 4.20(1H), 4.36(1H), 6.81–7.50(4H) |
| 24 | 1.0–1.8(6H), 1.85–2.38(6H), 2.03(3H), 2.20(3H), 2.7–3.0(4H), 3.61(3H), 4.30(1H), 4.38(1H), 6.82–7.38(4H) |
| 25 | 1.05–1.80(6H), 1.31(9H), 1.82–2.45(6H), 2.72–3.07(4H), 4.22(1H), 5.4–12.3(2H), 6.86–7.40(5H) |
| 26 | 1.13–2.42(14H), 2.06(3H), 2.11(3H), 2.50–2.93(4H), 3.62(3H), 4.37(1H), 4.42(1H), 6.82–7.13(2H), 7.16–7.43(2H) |
| 27* | 0.80–1.67(6H), 1.90–2.56(4H), 2.09(3H), 2.31(3H), 2.34(3H), 3.4(1H), 4.59(1H), 6.90–7.35(4H), 8.79(1H), 10.46(1H) |
| 28 | 1.00–1.77(6H), 1.85–2.40(4H), 4.66(1H), 6.60–8.00(1H), 6.80–7.10(2H), 7.20–7.69(4H), 7.83(1H), 8.20–8.52(1H), 9.16–9.35(1H), 9.40–10.35(1H), 10.17(1H) |
| 29* | 0.70–1.71(6H), 1.93–2.40(4H), 2.10(3H), 2.33(6H), 4.70(1H), 6.78–7.32(4H), 7.57(1H), 10.59(1H), 11.0–12.5(1H) |
| 30 | 0.90–1.82(6H), 1.22(3H), 1.88–2.65(4H), 2.10(3H), 2.44(3H), 2.51(3H), 4.07(2H), 4.56(1H), 5.21(1H), 6.84–7.48(4H), 10.61(1H) |
| 31 | 1.00–1.82(6H), 1.90–2.50(4H), 2.25(3H), 2.30(3H), 2.40(3H), 2.62(3H), 4.60(1H), 4.65(1H), 6.84–7.36(4H), 10.57(1H) |
| 32 | 1.00–1.75(6H), 1.85–2.60(4H), 2.07(3H), 2.21(3H), 2.24(3H), 2.60–3.70(2H), 4.38–4.73(2H), 6.75–7.40(6H) |
| 33 | 0.95–1.83(6H), 1.83–2.55(4H), 2.04(3H), 2.27(3H), 2.34(3H), 3.42(3H), 4.35–4.67(3H), 6.70–7.37(5H), 6.30–9.40(1H) |

TABLE 4-continued

| Comp. No. | NMR TMS Internal Standard δ (ppm) |
|---|---|
| 34 | 1.03-1.79(6H), 1.85-2.48(4H), 2.06(3H), 2.29(3H), 2.35(3H), 3.42(3H), 3.63(3H), 4.30-4.65(1H), 4.45(1H), 4.56(1H), 6.83-7.40(4H) |
| 35 | 1.06-1.77(6H), 1.90-2.45(4H), 2.03(3H), 2.10(3H), 2.20(3H), 2.45(3H), 4.37(1H), 4.5-10.0(1H), 6.81-7.38(4H) |
| 36 | 0.93(3H), 1.10-1.88(10H), 1.95-2.55(4H), 2.02(3H), 2.06(3H), 2.16(3H), 2.70(2H), 4.41(1H), 5.5-9.5(2H), 6.84-7.45(4H) |
| 37* | 0.95-1.80(6H), 1.90-2.42(4H), 2.04(3H), 2.18(3H), 2.26(3H), 4.44(1H), 6.5(1H), 6.82-7.36(4H), 8.37(1H) |
| 38 | 0.90-1.65(6H), 1.90-2.38(5H), 2.40-2.65(5H), 2.68-2.95(2H), 3.0-3.7(2H), 4.49(1H), 6.5-10.0(2H), 6.85-7.35(4H) |
| 39 | 0.93-2.44(12H), 2.12(3H), 2.44-2.68(2H), 2.52(3H), 2.68-3.05(2H), 4.50(1H), 6.0-9.2(2H), 6.83-7.35(4H) |
| 40 | 0.81(3H), 1.02-2.70(14H), 2.05(3H), 2.11(3H), 2.22(3H), 4.48(1H), 5.3-5.9(1H), 6.33(1H), 5.9-9.0(1H), 6.8-7.4(4H) |
| 41 | 0.90-1.83(6H), 1.83-2.50(4H), 2.07(3H), 2.20(3H), 2.28(3H), 2.38(3H), 4.49(1H), 4.8-8.7(2H), 6.16(1H), 6.85-7.40(4H), 7.72(1H) |
| 42 | 0.90-1.80(6H), 1.21(3H), 1.80-2.56(4H), 2.09(3H), 2.20(3H), 2.28(3H), 2.38(3H), 4.09(2H), 4.48(1H), 5.29(1H), 6.15(1H), 6.85-7.42(4H), 7.72(1H) |
| 43 | 1.00-1.78(6H), 2.00-2.42(4H), 2.10(3H), 2.21(6H), 4.48(1H), 5.5-9.0(3H), 6.76-7.35(4H) |
| 44 | 1.05-1.78(6H), 2.00-2.40(4H), 2.06(3H), 2.21(3H), 2.29(3H), 3.76(2H), 4.50(1H), 6.83-7.40(4H), 7.5-10.0(3H) |
| 45 | 0.96-1.90(6H), 1.95-2.50(4H), 2.06(3H), 2.25(3H), 2.31(3H), 2.98(2H), 3.72(2H), 4.50(1H), 4.9(3H), 6.85-7.40(4H) |
| 46 | 1.00-1.81(6H), 1.83-2.45(4H), 2.58(3H), 4.38(1H), 6.00-8.30(2H), 6.83-7.56(7H), 7.75-8.20(2H) |
| 47 | 0.95-1.80(6H), 1.90-2.43(4H), 2.03(3H), 2.18(3H), 2.28(3H), 4.44(1H), 5.0-7.5(3H), 6.82-7.36(4H), 8.37(1H) |
| 48 | 1.00-1.83(6H), 1.88-2.51(4H), 2.06(3H), 2.16(3H), 2.25(3H), 4.46(1H), 6.83-7.12(2H), 7.13-7.41(2H), 7.67(1H), 8.26(3H) |
| 49 | 1.00-1.76(6H), 1.86-2.45(4H), 2.04(3H), 2.14(E or Z) and 2.30(E or Z)(3H) 2.21(3H), 3.87(E or Z) and 3.95(E or Z)(3H), 4.50(1H), 6.0-9.5(2H), 6.80-7.38(4H), 7.53(Z) and 8.30(E)(1H) |
| 50 | 1.00-1.78(9H), 1.90-2.45(4H), 2.04(3H), 2.13(E or Z) and 2.29(E or Z)(3H), 4.0-4.4(2H), 4.44(1H), 5.5-8.5(2H), 6.80-7.40(4H) 7.54(Z) and 8.32(E)(1H) |
| 51 | 0.95(3H), 1.09-1.82(10H), 2.00-2.50(4H), 2.06(3H), 2.13(E or Z) and 2.30(E or Z)(3H), 2.22(3H), 3.96-4.26(2H), 4.45(1H), 6.5-9.5(2H), 6.83-7.38(4H), 7.54(Z) and 8.33(E)(1H) |
| 52 | 1.0-1.86(6H), 1.88-2.50(13H), 4.30-4.75(3H), 5.06-5.50(2H), 5.5-7.5(2H), 6.0(1H), 6.83-7.40(4H), 7.56(Z) and 8.36(E)(1H) |
| 53 | 0.90-1.76(6H), 1.78-2.45(13H), 4.40(1H), 6.23(Z) and 6.33(E)(1H), 5.7-9.0(2H), 6.85-7.53(14H), 7.65(Z) and 8.53(E)(1H) |
| 54* | 1.95-1.76(6H), 1.90-2.35(4H), 2.10(3H), 2.16(3H), 3.56(2H), 4.45(1H), 6.6(2H), 6.80-7.37(4H) |
| 55* | 1.00-1.85(6H), 1.90-2.42(4H), 2.10(3H), 2.18(3H), 2.55-3.04(4H), 4.49(1H), 6.2(2H), 6.76-7.42(4H) |
| 56 | 1.05-1.78(6H), 1.21(9H), 1.82-2.43(4H), 4.16(1H), 6.69(1H), 6.82(1H), 6.60-7.80(7H) |
| 57 | 1.00-1.80(6H), 1.85-2.40(4H), 2.07(3H), 2.12(3H), 4.44(1H), 6.55(1H), 6.68-7.38(4H), 7.0(3H) |
| 58 | 1.02-2.94(18H), 2.10(3H), 2.16(3H), 3.16(3H), 3.61(3H), 4.50(1H), 6.77-7.40(4H) |
| 59 | 0.80-2.40(12H), 2.22(3H), 2.40-2.95(4H), 2.48(3H), 3.33(3H), 3.64(3H), 4.58(1H), 6.77-7.30(4H) |
| 60 | 0.96-1.83(6H), 1.84-2.70(4H), 2.29(3H), 2.30(3H), 2.40(3H), 3.30(3H), 3.63(3H), 4.60(1H), 6.80-7.30(4H), 10.61(1H) |
| 61 | 1.00-1.77(6H), 1.77-2.66(4H), 2.26(6H), 2.43(3H), 4.46(2H), 4.73(1H), 5.09(2H), 6.77-7.60(4H), 7.35(10H), 10.63(1H) |
| 62 | 0.95-2.50(10H), 1.53(3H), 1.59(1H), 2.19(6H), 2.36 and 2.38(3H), 3.31(3H), 3.63(3H), 4.52(1H), 5.42(1H), 6.79-7.33(4H) |
| 63 | 0.95-2.60(11H), 1.54(3H), 2.11(3H), 2.22(3H), 2.40(3H), 4.45(2H), 4.74(1H), 5.07(2H), 5.40(1H), 6.75-7.50(4H), 7.34(10H) |
| 64 | 0.90-1.83(6H), 1.85-2.70(4H), 2.01(3H), 2.10(3H), 2.16(3H), 2.62(3H), 3.28(3H), 3.63(3H), 4.51(1H), 6.77-7.35(4H) |
| 65 | 0.86(3H), 1.00-2.65(17H), 2.20(6H), 2.38(3H), 3.30(3H), 3.63(3H), 4.60(1H), 5.21(1H), 6.78-7.37(4H) |
| 66 | 0.94(3H), 1.08-1.85(10H), 1.88-2.50(4H), 2.00(3H), 2.07(3H), 2.15(3H), 2.27(3H), 2.65(2H), 3.65(3H), 4.50(1H), 6.82-7.39(4H) |
| 67 | 0.60-1.79(11H), 1.88-2.50(15H), 3.30(3H), 3.63(3H), 4.57(1H), 5.20-5.90(1H), 6.27(1H), 6.79-7.38(4H) |
| 68 | 0.95-1.78(6H), 1.83-2.43(4H), 2.14(3H), 2.23(3H), 2.31(3H), 4.42(2H), 4.65(1H), 5.09(2H), 5.5-6.5(1H), 6.77-7.53(4H), 7.36(10H) |

*: DMSO-$d_6$

EXAMPLE 23

Example of Pharmaceutical Composition

| A) Capsule | |
|---|---|
| (1) Compound 21 | 50 mg |
| (2) Fine powder cellulose | 30 mg |
| (3) Lactose | 37 mg |
| (4) Magnesium stearate | 3 mg |
| Total | 120 mg |

The above ingredients (1), (2), (3) and (4) were mixed and filled in a gelatin capsule.

| B) Soft Capsule | |
|---|---|
| (1) Compound 16 | 50 mg |
| (2) Corn oil | 100 mg |
| Total | 150 mg |

The above ingredients (1) and (2) were mixed and filled in a soft capsule.

| C) Tablet | |
|---|---|
| (1) Compound 27 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Potassium carboxy methylcellulose | 20 mg |
| Total | 120 mg |

According to a conventional manner, these ingredients were mixed and compressed with a tablet machine.

The following Experiments illustrate the pharmacological activities of the phenol derivatives of the general formula (I).

EXPERIMENT 1

Thromboxane $A_2$ (TXA$_2$) receptor antagonism

Inhibitory effect on contraction of rabbit aorta by thromboxan $A_2$ (TXA$_2$)-mimics Method: A spiral strip of the rabbit aorta (2-3 mm wide, about 3 cm long) was suspended in Krebs-Henseleit solution under the load of 2 g. The Krebs-Henseleit solution was saturated with a mixed gas of 95%$O_2$-5%$CO_2$ and warmed at 37° C. Inhibition of the contraction of the vascular strip caused by a TXA$_2$ mimic substance U-44069[1] ($10^{-7}$M) or U-46619[2] ($3\times10^{-8}$M), by pretreatment with Compound No. 13 30 minutes before was studied.
1) U-44069: (5Z, 9α, 11α, 13E, 15S)-15-hydroxy-9,11-(epoxymethano)-prosta-5,13-dienoic acid (manufactured by The Upjohn Company in U.S.A.)
2) U-46619: (5Z, 9α, 11α, 3E, 15S)-15-hydroxy-11,9-(epoxymethano)-prosta-5,13-dienoic acid (manufactured by Cayman Chemical Company)

Results: The results are shown in Table 5. In Table 5, "*" represents addition of U-46619.

TABLE 5

| Comp. No. | Inhibition (%) | | |
|---|---|---|---|
| | $10^{-5}$M | $10^{-6}$M | $10^{-7}$M |
| 1 | 100 | 56 | — |
| 9 | 100 | 27 | — |
| 21 | — | 99 | 5 |
| 22 | 100 | 45 | — |
| 12 | 100 | 79 | 12 |
| 17 | — | 98 | 12 |
| 27 | — | — | 98 |
| 32* | — | 100 | 95 |
| 37* | — | — | 100 |
| 35* | — | 98 | 23 |
| 52* | — | — | 96 |

EXPERIMENT 2

Inhibition of specific [$^3$H] U-46619 binding to guinea pig platelet membrane

Method: Blood from normal guinea pig was collected into 0.315% citrate solution containing aspirin (final concentration 1 mM) and was centrifuged at 3000 r.p.m. for 5 to 6 sec. The PRP (platelet rich plasma) was centrifuged at 4800 r.p.m for 10 min. at 4° C. Platelet membranes were prepared according to the following procedure: In order to remove the residual plasma protein, the platelet pellet was washed once with 30 ml of buffer containing 25 mM Tris-HCl/5 mM MgCl$_2$ (pH 7.4) and recentrifuged to pellet the platelets. The platelets were then resuspended in 20 ml of the same buffer, and the cells were disrupted by sonication. The sonication was performed on ice using a Kontes Sonicator (Vineland, N.J.). The platelets were sonicated for a total of 90 sec. with a 15 sec. burst followed by a 15 sec. intermission. The sonicated mixture was centrifuged at 100,000×g for 1 hour and the membrane fraction was suspended in the same buffer. The protein concentration was adjusted to 1 mg/ml.

The binding assay was performed at 25° C. for 30 min. One ml of the resuspended membrane fraction was incubated with 4 mM of [$^3$H] U-46619. The incubation mixture was filtered through a glass fiber membrane (GF/C, whatman) to separate the membrane bound from free [$^3$H] U-46619. The membranes were quickly washed twice with 5 ml of cold buffer, mixed with 4 ml of ACS scintillation fluid and counted for [$^3$H] U-46619.

Results: The results are shown in Table 6.

TABLE 6

| Comp. No. | IC$_{50}$ (M) (Concentration for 50% inhibition) |
|---|---|
| 1 | $2.4 \times 10^{-7}$ |
| 9 | $1.3 \times 10^{-7}$ |
| 19 | $1.6 \times 10^{-7}$ |
| 21 | $4.9 \times 10^{-8}$ |
| 22 | $1.6 \times 10^{-7}$ |
| 12 | $2.0 \times 10^{-7}$ |
| 17 | $8.4 \times 10^{-7}$ |
| 27 | $2.3 \times 10^{-9}$ |
| 32 | $3.2 \times 10^{-8}$ |
| 37 | $1.3 \times 10^{-8}$ |
| 35 | $8.0 \times 10^{-8}$ |
| 52 | $1.4 \times 10^{-8}$ |

EXPERIMENT 3

Inhibitory effect on U-46619 (TXA$_2$ mimic)-induced broncho-constriction in guinea pig Method: Eight male Hartley guinea pigs were used per one group. The guinea pig anesthetized with urethane (1.5 g/kg, i.p.) was fixed in a dorsal position, subjected to tracheotomy and connected to a respirator through a cannula. A side branch of the tracheal cannula was connected to a respirator (Harvard apparatus rodent respirator Type 680) at the rate of 70 strokes/min. and a constant volume of 3 to 5 ml.

Inflation pressure was kept constant at 10 cm H$_2$O.

After treatment with gallamine triethiodide (1 mg/kg, i.v.), U-46619 (10 µg/Kg) dissolved in a physiological saline solution was given through a carotid cannula and the airway resistance was measured by the overflow technique of Konzett-Rossler method (Konzett, H. and Rössler, R., Naunyn-Schmiedegerg's Arch, Exp. Path. Pharmak., 195, 71-74 (1940). A test compound was suspended in 5% gum arabic solution and was administered orally 1 hour before the treatment with U-46619.

Alternatively, a test compound was dissolved in aqueous 50% dimethylsulfoxide solution and administered interveneously in the dosage of 0.1 ml/100 g body weight 9 minutes before the treatment of U-46619.

Results: The results are shown in Table 7.

TABLE 7

| Comp. No. | Dose (mg/kg) | Route of administration | Number of animals | % Inhibition |
|---|---|---|---|---|
| 1 | 5 | p.o. | 7 | 55** |
| 9 | 0.31 | i.v. | 5 | 65** |
| 21 | 5 | p.o. | 9 | 76** |
| 21 | 0.31 | i.v. | 5 | 51** |
| 22 | 5 | p.o. | 7 | 83** |
| 22 | 1.25 | i.v. | 5 | 43** |
| 12 | 0.31 | i.v. | 4 | 96** |
| 17 | 1.25 | i.v. | 6 | 71** |
| 27 | 5 | p.o. | 10 | 84** |
| 32 | 0.31 | p.o. | 7 | 57** |
| 37 | 1.25 | p.o. | 7 | 59** |
| 35 | 5 | p.o. | 6 | 76** |
| 52 | 0.31 | p.o. | 7 | 36** |

**: $p < 0.01$ vs control group

EXPERIMENT 4

Inhibitory action on lipid peroxides production in rat brain homogenates

Method: The male SD rat brain tissue was used as 5% homogenate in phosphate-buffered solution. After incubation of the homogenate for 1 hour at 37° C., the amount of lipid peroxides produced was determined by the thiobarbituric acid method according to the description of Ohkawa et al. (Analytical Biochemistry, 95: 551, 1979)

Test compounds were used as a solution of dimethylsulfoxide. The inhibitory action on lipid peroxide production was expressed as a % inhibition as compared with the amount of production in the vehicle group.

Results: The results are shown in Table 8. As seen from Table 8, the test compound markedly inhibited the lipid peroxidation.

TABLE 8

| Comp. No. | Inhibition (%) |
|---|---|
| 1 | 92.0 |
| 6 | 100 |
| 9 | 100 |
| 56 | 100 |
| 5 | 100 |
| 12 | 100 |
| 20 | 74.5 |

(The concentration of each test compound is $10^{-5}$M.)

EXPERIMENT 5

5-Lipoxygenase inhibitory activity

Method: $10^7$ RBL-1 cells (rat basophilic leukemia cells) were suspended in 0.5 ml of MCM (mast cell medium), and test solutions (made up of 0.5 ml of MCM, 50 μg of arachidonic acid, 10 μg of A-23187 (calcium ionophore) and 1 μM, 0.01 μM and 0.001 μM as the final concentration of the phenol compound, respectively) prepared previously were added respectively to the suspension, followed by reaction at 37° C. for 20 minutes. After the conclusion of the reaction, 4 ml of ethanol and 1,4-dimethoxy-2-methyl-3-(3-methoxypropyl)naphthalene as the internal reference drug were added to the reaction solution, and the mixture was shaken thoroughly and allowed to stand at room temperature for 10 minutes. Then, it was centrifuged (2000 r.p.m.) for 10 minutes, and the supernatant fluid was separated and concentrated to dryness under reduced pressure. 0.5 ml of 60% aqueous methanol was added to the concentrate, and 100 μl of the resulting solution was taken and subjected to high-performance liquid chromatography to determine the amount of 5-HETE (5-hydroxy-eicosatetraenoic acid). Determination of 5-HETE was made through measurement of an absorption at 237 nm with a UV absorption monitor.

The 5-HETE production inhibitory effect (IE) was expressed by $$1 - \frac{b}{a} \times 100,$$

wherein a is a peak height or peak area corrected by the peak for the internal reference when the phenol compound is not contained; b is a peak height or peak area corrected by the peak for the internal reference when the phenol compound is contained.

Results: The results are shown in Table 9.

TABLE 9

| Comp. No. | Inhibitory effect on 5-HETE production (%) Concentration of test compound | | |
|---|---|---|---|
| | $10^{-5}$M | $10^{-6}$M | $10^{-7}$M |
| 57 | 100 | 90 | 27 |
| 56 | 93 | 93 | 66 |
| 12 | 96 | 22 | — |

EXPERIMENT 6

Angiogenesis inhibitory activity

Method: Shell-less chorioallantoic membrane assay. The shell-less chorioallantoic membrane (CAM) assay was carried out by the method of Taylor and Folkman [S. Taylor and J. Folkman; Nature, 297, 307 (1982)] with a slight modification. Thus, 3-day chick embryos were removed from their shells and cultured in plastic cups on hammocks of plastic wrap. Samples along with ECGS (endothelial cell growth supplements, Collaborative Research Inc.) were placed on plastic disks (polypropylene, 6 mm in diameter). After the solution had dried, the disks were placed on the CAM of 10-day embryos. Three days later, inhibition of the neovascular formation by fumagillin was observed under a stereoscope (×20, SMZ-10, Nikon), and compared to the control disk containing ECGS as a stimulant of angiogenesis without samples.

Results: The results are shown in Table 10

TABLE 10

| Comp. No. | Dose (μg) | Number of disks tested | Number of disks showing angiogenesis inhibition | Evaluation |
|---|---|---|---|---|
| 1 | 20 | 6 | 6 | ++ |
| | 4 | 6 | 3 | +++ |

+: effective at 100 μg; ++: effective at 20 μg; +++: effective at 4 μg

EXPERIMENT 7

Extension of bleeding time

Method: Test compounds were administered orally to rats one hour before the experiments. The rats were anesthetized and the tail was cut at 1.5 mm from the tip. Immediately, the tail was hung down into a physiological saline warmed at 37° C. The time required from initiation to stop of bleeding (bleeding time) was measured.

Results: The results are shown in Table 11.

TABLE 11

| Comp. No. | Dose (mg/kg) | Bleeding time (sec.) | Control (sec.) |
|---|---|---|---|
| 21 | 30 | 529 ± 154** | 164 ± 27 |
| | 10 | 235 ± 38 | 173 ± 23 |
| 12 | 30 | 258 ± 14** | 164 ± 27 |
| | 10 | 272 ± 52* | 173 ± 23 |

Each group contains 5 animals.
*: $p < 0.05$. **: $p < 0.01$ degree of confidence to the control group

EXPERIMENT 8

Inhibitory effect of vasoconstriction by PGD$_2$

Method: A spiral strip of the rabbit aorta (2-3 mm wide, about 3 cm long) was suspended in Krebs-Henseleit solution under the load of 2 g. The Krebs-Henseleit solution was saturated with a mixed gas of 95% $O_2$-5% $CO_2$ and warmed at 37° C. Inhibition of the contraction of the vascular strip caused by addition of PGD$_2$ ($3 \times 10^{-6}$M) by pretreatment with Compound No. 13 30 minutes before was studied.

Result: The results are shown in Table 12.

TABLE 12

| Comp. No. | Concentration (M) | Inhibitory Rate (%) |
|---|---|---|
| 21 | $10^{-7}$ | 54 (n = 2) |
| 27 | $10^{-7}$ | 100 (n = 2) |

"n" is the number of runs.

What is claimed is:

1. A compound of the formula:

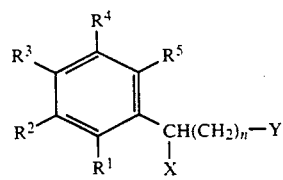

wherein
R$^1$ is hydroxyl;
R$^2$ is hydrogen, hydroxyl, alkyl having 1 to 4 carbon atoms or alkoxy having 1 to 4 carbon atoms;
R$^3$ is hydrogen, hydroxyl, alkyl having 1 to 8 carbon atoms unsubstituted or substituted with
hydroxyl,
alkoxy having 1 to 4 carbon atoms,
halogen or
carboxyl,
aralkyl having 7 to 13 carbon atoms unsubstituted or substituted with 1 to 5 halogen atoms, halogen, formyl, 1,3-dioxolan, propylene acetal, 1,3-oxathiolan, di(C$_{1-4}$)alkyl acetal, acyl having 2 to 7 carbon atoms, carboxyl, alkoxycarbonyl having 2 to 5 carbon atoms, aralkyloxycarbonyl having 8 to 10 carbon atoms, aryloxycarbonyl having 7 to 10 carbon atoms, aminocarbonyl, (C$_{1-4}$)alkylaminocarbonyl, morpholinocarbonyl unsubstituted or substituted with (C$_{1-2}$)alkyl or (C$_{1-2}$)alkoxy, piperidinocarbonyl unsubstituted or substituted with (C$_{1-2}$)alkyl or (C$_{1-2}$)alkoxy, pyrrolidinocarbonyl unsubstituted or substituted with (C$_{1-2}$)alkyl or (C$_{1-2}$)alkoxy, piperazinocarbonyl unsubstituted or substituted with (C$_{1-2}$)alkyl or (C$_{1-2}$)alkoxy, —CH=R$^6$ wherein
R$^6$ is (C$_{1-4}$)alkyl or (C$_{2-6}$)acyl or
—CH=NR$^7$ wherein
R$^7$ is hydroxyl, (C$_{1-8}$)alkoxy, (C$_{2-6}$)alkenyloxy or benzhydryloxy;
R$^4$ is alkyl having 1 to 8 carbon atoms unsubstituted or substituted with
hydroxyl,
alkoxy having 1 to 4 carbon atoms,
halogen or
carboxyl,
aralkyl having 7 to 13 carbon atoms unsubstituted or substituted with 1 to 5 halogen atoms, halogen, formyl, 1,3-dioxolan, propylene acetal, 1,3-oxathiolan, di(C$_{1-4}$)alkyl acetal, acyl having 2 to 7 carbon atoms, carboxyl, alkoxycarbonyl having 2 to 5 carbon atoms, aralkyloxycarbonyl having 8 to 10 carbon atoms, aryloxycarbonyl having 7 to 10 carbon atoms, aminocarbonyl, (C$_{1-4}$)alkylaminocarbonyl, morpholinocarbonyl unsubstituted or substituted with (C$_{1-2}$)alkyl or (C$_{1-2}$)alkoxy, piperidinocarbonyl unsubstituted or substituted with (C$_{1-2}$)alkyl or (C$_{1-2}$)alkoxy, pyrrolidinocarbonyl unsubstituted or substituted with (C$_{1-2}$)alkyl or (C$_{1-2}$)alkoxy, piperazinocarbonyl unsubstituted or substituted with (C$_{1-2}$)alkyl or (C$_{1-2}$)alkoxy, —CH=R$^6$ wherein
R$^6$ is (C$_{1-4}$)alkyl or (C$_{2-6}$)acyl or
—CH=NR$^7$ wherein
R$^7$ is hydroxyl, (C$_{1-8}$)alkoxy, (C$_{2-6}$)alkenyloxy or benzhydryloxy;

R$^5$ is hydrogen or alkyl having 1 to 4 carbon atoms; or two adjacent groups of R$^2$, R$^3$, R$^4$ and R$^5$ may bond to each other to form
—(CH$_2$)$_a$— wherein a is 3 or 4,
—CH=CH—CH=—,
—(CH$_2$)$_b$—CO— wherein b is 2 or 3 or
—(CH$_2$)l—CO—O— wherein l is 1 or 2;
X is phenyl unsubstituted or substituted with halogen, alkyl having 1 to 4 carbon atoms or alkoxy having 1 to 4 carbon atoms at the para-position thereof or thienyl;
Y is carboxyl or alkoxycarbonyl having 2 to 4 carbon atoms; and
n is an integer of 3 to 15.

2. A compound according to claim 1, wherein
R$^1$ and R$^2$ are as defined in claim 1,
R$^3$ is hydrogen; hydroxyl; alkyl having 1 to 8 carbon atoms; aralkyl having 7 to 13 carbon atoms; halogen; or formyl,
R$^4$ is alkyl having 1 to 8 carbon atoms unsubstituted or substituted with hydroxyl, alkoxy having 1 to 4 carbon atoms or carboxyl; aralkyl having 7 to 13 carbon atoms unsubstituted or substituted with 1 to 5 halogen atoms; halogen; formyl; acyl having 2 to 7 carbon atoms; carboxyl; —CH=R$^6$ wherein R$^6$ is as defined in claim 1; or —CH=NR$^7$ wherein R$^7$ is as defined in claim 1,
R$^5$ is as defined in claim 1,
or two adjacent groups of R$^2$, R$^3$, R$^4$ and R$^5$ may bond to each other to form —(CH$_2$)$_a$— wherein a is 3 or 4, —CH=CH—CH=CH— or —(CH$_2$)$_b$—CO— wherein b is 2 or 3,
X is phenyl unsubstituted or substituted with halogen or alkyl having 1 to 4 carbon atoms at the para-position thereof,
Y is as defined in claim 1, and
n is as defined in claim 1.

3. A compound according to claim 1, wherein X is phenyl, 4-methylphenyl, 4-fluorophenyl, 2-thienyl or 3-thienyl, Y is carboxyl and n is an integer of 5 to 9.

4. A compound according to claim 3, wherein X is 4-fluorophenyl.

5. A compound according to claim 4, wherein R$^1$ is hydroxy; R$^2$, R$^3$ and R$^5$ are methyl; R$^4$ is formyl; and n is 5.

6. A compound according to claim 4, wherein R$^1$ is hydroxy; R$^2$, R$^3$ and R$^5$ are methyl; R$^4$ is hydroxymethyl; and n is 5.

7. A compound according to claim 4, wherein R$^1$ is hydroxy; R$^2$, R$^3$ and R$^5$ are methyl; R$^4$ is acetyl; and n is 5.

8. A compound according to claim 4, wherein R$^1$ is hydroxy; R$^2$, R$^3$ and R$^5$ are methyl; R$^4$ is —CH=NOCH$_2$CH=CH$_2$; and n is 5.

9. A compound according to claim 4, wherein R$^1$ is hydroxy; R$^2$ and R$^3$ are methyl; R$^4$ together with R$^5$ forms —CO—(CH$_2$)$_2$—; and n is 5.

10. A compound according to claim 4, wherein R$^1$ is hydroxy; R$^2$ and R$^5$ are methyl; R$^4$ together with R$^3$ forms —(CH$_2$)$_3$—; and n is 5.

11. A pharmaceutical composition comprising as an active ingredient a compound of the formula:

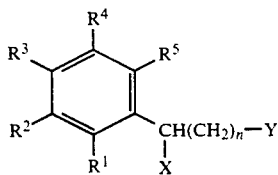

(I)

wherein
$R^1$ is hydroxyl;
$R^2$ is hydrogen, hydroxyl, alkyl having 1 to 4 carbon atoms or alkoxy having 1 to 4 carbon atoms;
$R^3$ is hydrogen, hydroxyl, alkyl having 1 to 8 carbon atoms unsubstituted or substituted with
hydroxyl,
alkoxy having 1 to 4 carbon atoms,
halogen or
carboxyl,
aralkyl having 7 to 13 carbon atoms unsubstituted or substituted with 1 to 5 halogen atoms, halogen, formyl, 1,3-dioxolan, propylene acetal, 1,3-oxathiolan, di($C_{1-4}$)alkyl acetal, acyl having 2 to 7 carbon atoms, carboxyl, alkoxycarbonyl having 2 to 5 carbon atoms, aralkyloxycarbonyl having 8 to 10 carbon atoms, aryloxycarbonyl having 7 to 10 carbon atoms, aminocarbonyl, ($C_{1-4}$)alkylaminocarbonyl, morpholinocarbonyl unsubstituted or substituted with ($C_{1-2}$)alkyl or ($C_{1-2}$)alkoxy, piperidinocarbonyl unsubstituted or substituted with ($C_{1-2}$)alkyl or ($C_{1-2}$)alkoxy, pyrrolidinocarbonyl unsubstituted or substituted with ($C_{1-2}$)alkyl or ($C_{1-2}$)alkoxy, piperazinocarbonyl unsubstituted or substituted with ($C_{1-2}$)alkyl or ($C_{1-2}$)alkoxy, —CH=$R^6$ wherein
$R^6$ is ($C_{1-4}$)alkyl or ($C_{2-6}$)acyl or
—CH=$NR^7$ wherein
$R^7$ is hydroxyl, ($C_{1-8}$)alkoxy, ($C_{2-6}$)alkenyloxy or benzhydryloxy;
$R^4$ is alkyl having 1 to 8 carbon atoms unsubstituted or substituted with
hydroxyl,
alkoxy having 1 to 4 carbon atoms,
halogen or
carboxyl,
aralkyl having 7 to 13 carbon atoms unsubstituted or substituted with 1 to 5 halogen atoms, halogen, formyl, 1,3-dioxolan, propylene acetal, 1,3-oxathiolan, di($C_{1-4}$)alkyl acetal, acyl having 2 to 7 carbon atoms, carboxyl, alkoxycarbonyl having 2 to 5 carbon atoms, aralkyloxycarbonyl having 8 to 10 carbon atoms, aryloxycarbonyl having 7 to 10 carbon atoms, aminocarbonyl, ($C_{1-4}$)alkylaminocarbonyl, morpholinocarbonyl unsubstituted or substituted with ($C_{1-2}$)alkyl or ($C_{1-2}$)alkoxy, piperidinocarbonyl unsubstituted or substituted with ($C_{1-2}$)alkyl or ($C_{1-2}$)alkoxy, pyrrolidinocarbonyl unsubstituted or substituted with ($C_{1-2}$)alkyl or ($C_{1-2}$)alkoxy, piperazinocarbonyl unsubstituted or substituted with ($C_{1-2}$)alkyl or ($C_{1-2}$)alkoxy, —CH=$R^6$ wherein
$R^6$ is ($C_{1-4}$)alkyl or ($C_{2-6}$)acyl or
—CH=$NR^7$ wherein
$R^7$ is hydroxyl, ($C_{1-8}$)alkoxy, ($C_{2-6}$)alkenyloxy or benzhydryloxy;
$R^5$ is hydrogen or alkyl having 1 to 4 carbon atoms; or two adjacent groups of $R^2$, $R^3$, $R^4$ and $R^5$ may bond to each other to form
—$(CH_2)_2$— wherein a is 3 or 4,
—CH=CH—=CH—,
—$(CH_2)_b$—CO— wherein b is 2 or 3 or
—$(CH_2)_l$—CO—O— wherein l is 1 or 2,
X is phenyl unsubstituted or substituted with
halogen,
alkyl having 1 to 4 carbon atoms or
alkoxy having 1 to 4 carbon atoms
at the para-position thereof or thienyl;
Y is carboxyl or alkoxycarbonyl having 2 to 4 carbon atoms; and
n is an integer of 3 to 15, and
a pharmaceutically acceptable carrier therefor.

12. A pharmaceutical composition according to claim 11, wherein the composition is a drug for treating and preventing cerebral, cardiac, renal and pulmonary circulatory system diseases; an antiasthmatic, an antiallergic or a drug for inhibiting vascularization.

13. A compound of the formula:

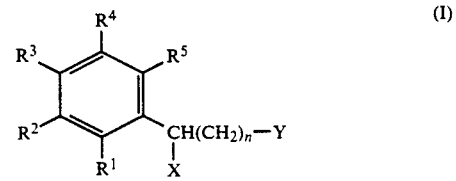

(I)

wherein
$R^1$ is hydroxyl;
$R^2$ is hydrogen, hydroxyl or alkyl having 1 to 4 carbon atoms;
$R^3$ is hydrogen, alkyl having 1 to 8 carbon atoms, halogen or formyl;
$R^4$ is alkyl having 1 to 8 carbon atoms unsubstituted or substituted with
hydroxyl,
alkoxy having 1 to 4 carbon atoms or
carboxyl,
aralkyl having 7 to 13 carbon atoms, halogen, formyl, acyl having 2 to 7 carbon atoms or carboxyl;
$R^5$ is hydrogen or alkyl having 1 to 4 carbon atoms; or
$R^2$ and $R^3$ may bond to each other to form —CH=CH—CH=CH—;
$R^3$ and $R^4$ may bond to each other to form
—$(CH_2)_a$— wherein a is 3 or 4,
—$(CH_2)_b$—CO— wherein b is 2 or 3 or
—$(CH_2)_l$—CO—O— wherein l is 1 or 2;
$R^4$ and $R^5$ may bond to each other to form
—$(CH_2)_a$— wherein a is 3 or 4 or
—$(CH_2)_b$—CO— wherein b is 2 or 3;
X is phenyl unsubstituted or substituted with
halogen or
alkyl having 1 to 4 carbon atoms
at the para-position thereof;
Y is carboxyl or alkoxycarbonyl having 2 to 4 carbon atoms; and
n is an integer of 3 to 15.

14. A process for producing a compound of the formula (I):

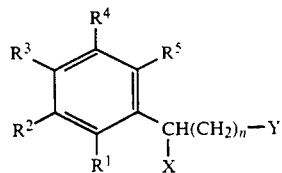

wherein
R$^1$ is hydroxyl,
R$^2$ is hydrogen, hydroxyl, alkyl having 1 to 4 carbon atoms or alkoxy having 1 to 4 carbon atoms;
R$^3$ is hydrogen, hydroxyl, alkyl having 1 to 8 carbon atoms unsubstituted or substituted with
hydroxyl,
alkoxy having 1 to 4 carbon atoms,
halogen or
carboxyl,
aralkyl having 7 to 13 carbon atoms unsubstituted or substituted with 1 to 5 halogen atoms, halogen, formyl, 1,3-dioxolan, propylene acetal, 1,3-oxathiolan, di(C$_{1-4}$)alkyl acetal, acyl having 2 to 7 carbon atoms, carboxyl, alkoxycarbonyl having 2 to 5 carbon atoms, aralkyloxycarbonyl having 8 to 10 carbon atoms, aryloxycarbonyl having 7 to 10 carbon atoms, aminocarbonyl, (C$_{1-4}$)alkylaminocarbonyl, morpholinocarbonyl unsubstituted or substituted with (C$_{1-2}$)alkyl or (C$_{1-2}$)alkoxy, piperidinocarbonyl unsubstituted or substituted with (C$_{1-2}$)alkyl or (C$_{1-2}$)alkoxy, pyrrolidinocarbonyl unsubstituted or substituted with (C$_{1-2}$)alkyl or (C$_{1-2}$)alkoxy, piperazinocarbonyl unsubstituted or substituted with (C$_{1-2}$)alkyl or (C$_{1-2}$)alkoxy, —CH=R$^6$ wherein
R$^6$ is (C$_{1-4}$)alkyl or (C$_{2-6}$)acyl or
—CH=NR$^7$ wherein
R$^7$ is hydroxyl, (C$_{1-8}$)alkoxy, (C$_{2-6}$)alkenyloxy or benzhydryloxy;
R$^4$ is alkyl having 1 to 8 carbon atoms unsubstituted or substituted with
hydroxyl,
alkoxy having 1 to 4 carbon atoms,
halogen or
carboxyl,
aralkyl having 7 to 13 carbon atoms unsubstituted or substituted with 1 to 5 halogen atoms, halogen, formyl, 1,3-dioxolan, propylene acetal, 1,3-oxathiolan, di(C$_{1-4}$)alkyl acetal, acyl having 2 to 7 carbon atoms, carboxyl, alkoxycarbonyl having 2 to 5 carbon atoms, aralkyloxycarbonyl having 8 to 10 carbon atoms, aryloxycarbonyl having 7 to 10 carbon atoms, aminocarbonyl, (C$_{1-4}$)alkylaminocarbonyl, morpholinocarbonyl unsubstituted or substituted with (C$_{1-2}$)alkyl or (C$_{1-2}$)alkoxy, piperidinocarbonyl unsubstituted or substituted with (C$_{1-2}$)alkyl or (C$_{1-2}$)alkoxy, pyrrolidinocarbonyl unsubstituted or substituted with (C$_{1-2}$)alkyl or (C$_{1-2}$)alkoxy, piperazinocarbonyl unsubstituted or substituted with (C$_{1-2}$)alkyl or (C$_{1-2}$)alkoxy, —CH=R$^6$ wherein
R$^6$ is (C$_{1-4}$)alkyl or (C$_{2-6}$)acyl or
—CH=NR$^7$ wherein
R$^7$ is hydroxyl, (C$_{1-8}$)alkoxy, (C$_{2-6}$)alkenyloxy or benzhydryloxy;

R$^5$ is hydrogen or alkyl having 1 to 4 carbon atoms; or two adjacent groups of R$^2$, R$^3$, R$^4$ and R$^5$ may bond to each other to form
—(CH$_2$)$_a$— wherein a is 3 to 4,
—CH=CH—CH=CH—,
—(CH$_2$)$_b$—CO— wherein b is 2 or 3 or
—(CH$_2$)l—CO—O— wherein l is 1 or 2;
X is phenyl unsubstituted or substituted with halogen,
alkyl having 1 to 4 carbon atoms or
alkoxy having 1 to 4 carbon atoms
at the para-position thereof or thienyl;
Y is carboxyl or alkoxycarbonyl having 2 to 4 carbon atoms; and
n is an integer of 3 to 15,
which process comprises reacting a compound of the formula:

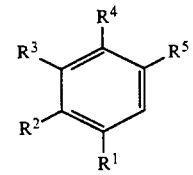

wherein R$^1$, R$^2$, R$^3$, R$^4$ and R$^5$ are as defined above, with a compound of the formula:

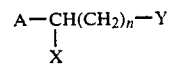

wherein X, Y and n are as defined above, and A is hydroxy, acetoxy, alkoxy having 1 to 4 carbon atoms or halogen.

15. A process for producing a compound of the formula (I):

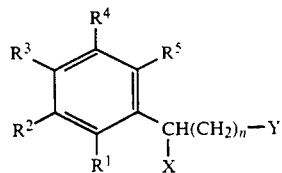

wherein
R$^1$ is hydroxyl;
R$^2$ is hydrogen, hydroxyl or alkyl having 1 to 4 carbon atoms;
R$^3$ is hydrogen, alkyl having 1 to 8 carbon atoms, halogen or formyl,
R$^4$ is alkyl having 1 to 8 carbon atoms unsubstituted or substituted with
hydroxyl,
alkoxy having 1 to 4 carbon atoms or
carboxyl,
aralkyl having 7 to 13 carbon atoms, halogen, formyl, acyl having 2 to 7 carbon atoms or carboxyl;
R$^5$ is hydrogen or alkyl having 1 to 4 carbon atoms; or
R$^2$ and R$^3$ may bond to each other to form —CH=CH—CH=CH—;
R$^3$ and R$^4$ may bond to each other to form
—(CH$_2$)$_a$— wherein a is 3 or 4,
—(CH$_2$)$_b$—CO— wherein b is 2 or 3 or
—(CH$_2$)l—CO—O— wherein l is 1 or 2;

$R^4$ and $R^5$ may bond to each other to form
—$(CH_2)_a$— wherein a is 3 or 4 or
—$(CH_2)_b$—CO— wherein b is 2 or 3;

X is phenyl unsubstituted or substituted with
halogen or
alkyl having 1 to 4 carbon atoms
at the para-position thereof;

Y is carboxyl or alkoxycarbonyl having 2 to 4 carbon atoms; and n is an integer of 3 to 15, which process comprises reacting a compound of the formula:

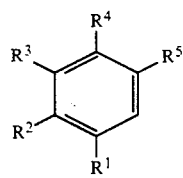   (II)

wherein $R^1$, $R^2$, $R^3$, $R^4$ and $R^5$ are as defined above, with a compound of the formula:

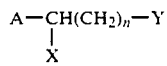   (III)

wherein X, Y and n are as defined above, and A is hydroxy, acetoxy, alkoxy having 1 to 4 carbon atoms or halogen.

16. A pharmaceutical composition comprising as an active ingredient a compound of the formula:

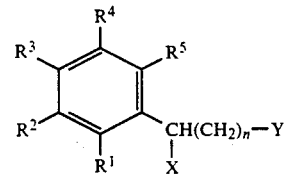   (I)

wherein
$R^1$ is hydroxyl;
$R^2$ is hydrogen, hydroxyl or alkyl having 1 to 4 carbon atoms;
$R^3$ is hydrogen, alkyl having 1 to 8 carbon atoms, halogen or formyl,
$R^4$ is alkyl having 1 to 8 carbon atoms unsubstituted or substituted with
hydroxyl,
alkoxy having 1 to 4 carbon atoms or
carboxyl,
aralkyl having 7 to 13 carbon atoms, halogen, formyl, acyl having 2 to 7 carbon atoms or carboxyl;
$R^5$ is hydrogen or alkyl having 1 to 4 carbon atoms; or
$R^2$ and $R^3$ may bond to each other to form —CH=CH—CH=CH—;
$R^3$ and $R^4$ may bond to each other to form
—$(CH_2)_a$— wherein a is 3 or 4,
—$(CH_2)_b$—CO— wherein b is 2 or 3 or
—$(CH_2)_l$—CO—O— wherein l is 1 or 2;
$R^4$ and $R^5$ may bond to each other to form
—$(CH_2)_a$— wherein a is 3 or 4 or
—$(CH_2)_b$—CO— wherein b is 2 or 3;
X is phenyl unsubstituted or substituted with
halogen or
alkyl having 1 to 4 carbon atoms
at the para-position thereof;
Y is carboxyl or alkoxycarbonyl having 2 to 4 carbon atoms; and
n is an integer of 3 to 15, and
a pharmaceutically acceptable carrier therefor.

* * * * *

UNITED STATES PATENT AND TRADEMARK OFFICE
CERTIFICATE OF CORRECTION

PATENT NO. :   5,162,571
DATED      :   November 10, 1992
INVENTOR(S):   SHIRAISHI et al.

It is certified that error appears in the above-identified patent and that said Letters Patent is hereby corrected as shown below:

On the title page, item [75], change "Suita" to

--Amagasaki--;

change "Mishikawa" to

--Nishikawa--.

item [30], as a second priority document add:

--May 2, 1988 [JP]    Japan .................... 63-109405--.

Signed and Sealed this

Twelfth Day of October, 1993

Attest:

BRUCE LEHMAN

Attesting Officer

Commissioner of Patents and Trademarks